United States Patent
Tietze et al.

(10) Patent No.: US 7,214,685 B2
(45) Date of Patent: May 8, 2007

(54) PRODRUGS FOR A SELECTIVE CANCER THERAPY

(75) Inventors: Lutz F. Tietze, Institut für Organische Chemie der Universität, Göttingen, Tammannstr. 2 37077 Göttingen (DE); Tobias Herzig, Marsstr 16A, 33739 Bielefeld (DE); Anja Fecher, Eisenbahnstr 16, 79576 Weil am Rhein (DE)

(73) Assignees: Lutz F. Tietze, Gottingen (DE); Tobias Herzig, Bielefeld (DE); Anja Fecher, Weil an Rhein (DE)

( * ) Notice: Subject to any disclaimer, the term of this patent is extended or adjusted under 35 U.S.C. 154(b) by 0 days.

(21) Appl. No.: 10/275,415

(22) PCT Filed: May 2, 2001

(86) PCT No.: PCT/EP01/04904

§ 371 (c)(1),
(2), (4) Date: Jun. 30, 2003

(87) PCT Pub. No.: WO01/83448

PCT Pub. Date: Nov. 8, 2001

(65) Prior Publication Data

US 2004/0033962 A1    Feb. 19, 2004

(30) Foreign Application Priority Data

May 2, 2000  (DE) ................................. 100 21 335
May 23, 2000  (DE) ................................. 100 25 329

(51) Int. Cl.
*A61K 31/403* (2006.01)
*A61K 31/437* (2006.01)
*C07D 209/82* (2006.01)
*C07D 209/94* (2006.01)
*C07D 221/12* (2006.01)

(52) U.S. Cl. ................ 514/298; 514/411; 546/108; 548/433; 548/439

(58) Field of Classification Search ............... 514/411, 514/298; 548/433, 439; 546/108
See application file for complete search history.

(56) References Cited

U.S. PATENT DOCUMENTS 5,646,298 A    7/1997    Powell

FOREIGN PATENT DOCUMENTS

WO    WO 97/44000    11/1997
WO    WO 98/11101    3/1998

OTHER PUBLICATIONS

Tietze, L.F. et al.: "Prodrugs of the cytostatic CC-1065 that can be activated in a tumor-selective manner" Angew. Chem. Int. Ed., Bd. 35, 1996, Seiten 2674-7, XP002183014 in der Anmeldung erwähnt das ganze Dokument.
Ling, Lei et al.: "A practical route to optically active CBI, a potent analog of the CC-1065 alkylation subunit". Heterocycl. Commun. (1997), 3(5), 405-408, 1997, XP001055518, s. Verbindung auf Seite 406.
Muratake, Hideaki et al.: "A novel phenol-forming reaction for preparation of benzene, furan, and thiophene analogs of CC-1065/ duocarmycin pharmacophores" Tetrahedron Lett. (1997, 28(43), 7577-7580, 1997, XP004125300, s. Verbindung 29 auf Seite 7579.
Aristoff, Paul A. et al.: "Synthesis and biochemical evaluation of the CBI-PDE-I-dimer, a benzannelated analog of (+)-CC-1065 that also produces delayed toxicity I mice". J. Med Chem. (1993), 36(14), 1956-63, 1993, XP000910185. s. Verbindung 12 auf Seite 1957.

*Primary Examiner*—Taofiq Solola
(74) *Attorney, Agent, or Firm*—Akerman & Senterfitt; Stephan A. Pendorf

(57) ABSTRACT

The chemotherapy of malignant tumours is greatly restricted by the generally slight differentiation of the available cytostatic agents between normal and malignant tissue. In order to achieve an improvement of the selectivity in cancer therapy, novel prodrugs have been developed from 6-hydroxy-2,3-dihydro-1H-indolene, 5-hydroxy-1,2-dihydro-3H-pyrrolo[3,2-e]indolene and 5-hydroxy-1,2-dihydro-3H-benzo[e]indolene as well as from 6-hydroxy-1,2,3,4-tetrahydro-benzo[f]-quinolines, that may be used within the framework of the ADEP therapy (antibody directed enzyme prodrug therapy). The new prodrugs are characterised by a high difference in toxicity between the prodrug and underlying drug and by a very high efficacy of the drug. After splitting off of the glycosidic and/or acetal group on the phenolic hydroxy groups of the prodrugs, a spirocyclopropacyclohexadiene is formed which, being a highly toxic group, effects an alkylation of the DNA or RNA.

9 Claims, 2 Drawing Sheets

PRODRUGS FOR A SELECTIVE CANCER THERAPY

CROSS REFERENCE TO RELATED APPLICATION

This application is a national stage of PCT/EP01/04904 filed May 2, 2001.

BACKGROUND OF THE INVENTION

1. Field of the Invention

It is known that cancer chemotherapeutic agents available at the present time produce undesirable side effects on account of their low selectivity, that limit the dose that can be applied or may even lead to a discontinuation of the treatment. The aim must therefore be to utilise genetic and phenotype differences between normal and malignant cells in order to achieve a higher selectivity.

2. Description of the Related Art

For this purpose prodrugs may be used that are either acid-catalysed by the pH value reduced by 1 to 2 units in tumour cells or that can be split within the scope of the ADEPT concept (antibody directed enzyme prodrug therapy), which is based on the utilisation of conjugates of glycohydrolases and monoclonal antibodies that bind to tumour-associated antigens [see Pharmacology & Therapeutics 83, 67–123, (1999); J. Biol. Chem. 272, 15804–15816, (1997); J. Med. Chem. 41, 1507–1512, (1998); Bioconjug. Chem. 98, 255–259, (1998); Cancer Immunol. Immunother. 44, 305–315, (1997)]. In this connection cytotoxic compounds are used that are detoxified by conversion into enzymatically splitable derivatives (prodrugs). The enzyme-antibody conjugates are selectively present, after their administration, on the surface of the cancer cells and split the prodrugs only in the tumour, with the release of the cytotoxic compound.

As cytotoxic compounds there have inter alia already been used derivatives of the seco-CI analogue of the natural substance CC-1065 that have been converted, inter alia as galactocides, into corresponding prodrugs. Glycohydrolases inter alia have been used for the antibody-enzyme conjugates [see Angew. Chem. 108, 2840–2842, (1996); Angew. Chem. Int. Ed. Engl. 35, 2674–2677, (1996)]. Essential criteria for the successful use of prodrugs within the framework of the ADEPT concept are the low toxicity of the prodrugs, a very high cytotoxicity of the underlying cytostatic agent, and a rapid splitting of the prodrug in the presence of the corresponding enzyme.

It is furthermore known that malignant cells exhibit an enhanced glycolysis and thus lactate production compared to normal tissue, and that the pH in the tumour tissue can be lowered by intravenously applied glucose [see S. Tanneberger, Experimentelle und klinische Tumorchemotherapie; Allgemeine Tumorchemotherapie; G. Fischer Verlag, Stuttgart/New York 1980; Naturwiss. 46, 2 (1959); Cancer Res. 42, 1498 (1982); 42, 1505 (1982); 49, 4373 (1989)].

It is also known that numerous glycohydrolases in a slightly acidic medium have a higher activity than at pH 7.4. Such glycohydrolases may also be bound to monoclonal antibodies that bind selectively to specific tumour-associated antigens on the membrane of malignant cells [see Pharmacology & Therapeutics 83, 67 (1999)].

In the past attempts have been made to utilise these differences in the pH value between normal tissue and tumour tissue for a selective tumour therapy [see Cancer Res. 49, 4179, (1989); Liebigs Ann. Chem. 847 (1987); Tetrahedron Lett. 22, 239, (1981); Angew. Chem. 102, 812, (1990); Liebigs Ann. Chem. 151, (1990)]. The acid-labile non-toxic prodrugs used for this purpose that are obtained from alkylating compounds have however proved not to be sufficiently acid-labile that they can be split selectively in the tumour tissue to form an active cytocidal agent.

Attempts have also been made to convert cytotoxic compounds by derivatisation into enzymatically splitable prodrugs having a reduced toxicity. With the previously synthesised compounds the problem arose that either the differences in the cytotoxicity of the prodrug and the underlying drug were not sufficient, and/or the drug was not sufficiently effective [see Angew. Chem. 108, 2840, (1996)].

In contrast to this the acid-catalysed prodrugs or prodrugs enzymatically splitable preferably with glycohydrolases proposed in the present invention that are obtained from 6-hydroxy-2,3-dihydro-1H-indolene, 5-hydroxy-1,2-dihydro-3H-pyrrolo[3,2-e]indolene and 5-hydroxy-1,2-dihydro-3H-benzo[e]indolene as well as from 6-hydroxy-1,2,3,4-tetrahydro-benzo[f]-quinoline derivatives unexpectedly exhibit a selectivity, not hitherto found, of more than 1:1500 between the prodrug and the cytostatic agent on which the prodrug is based, combined at the same time with a high cytotoxicity of the cytostatic agent in the cell culture.

SUMMARY OF THE INVENTION

The present invention relates to novel substituted 6-hydroxy-2,3-dihydro-1H-indoles of the general formula (I), novel substituted 5-hydroxy-1,2-dihydro-3H-pyrrolo[3,2-e] indoles of the general formula (II) and novel substituted 5-hydroxy-1,2-dihydro -3H-benzo[e]indoles of the general formula (III) as well as their O-glycosides with monosaccharides, disaccharides and oligosaccharides of the general formulae (IV), (V) and (VI), and novel O-glycosides with monosaccharides, disaccharides and oligosaccharides of 6-hydroxy-1,2,3,4-tetrahydro-benzo[f]-quinolines of the general formula (VII) as well as 6-hydroxy-1,2,3,4-tetrahydro-benzo[f]-quinolines of the general formula (VIII) according to claim 1, processes for their production according to claims 4 and 8, and their use as highly selective cytostatic agents in cancer therapy according to claims 9 and 10.

Advantageous embodiments of the new compounds and of the new process are described in the subclaims 2 and 3, and 5 to 7.

BRIEF DESCRIPTION OF THE DRAWINGS

Other objects, features and advantages of the present invention will become apparent upon reading the following detailed description, while referring to the attached drawings, in which.

DETAILED DESCRIPTION OF THE INVENTION

Figure 1:
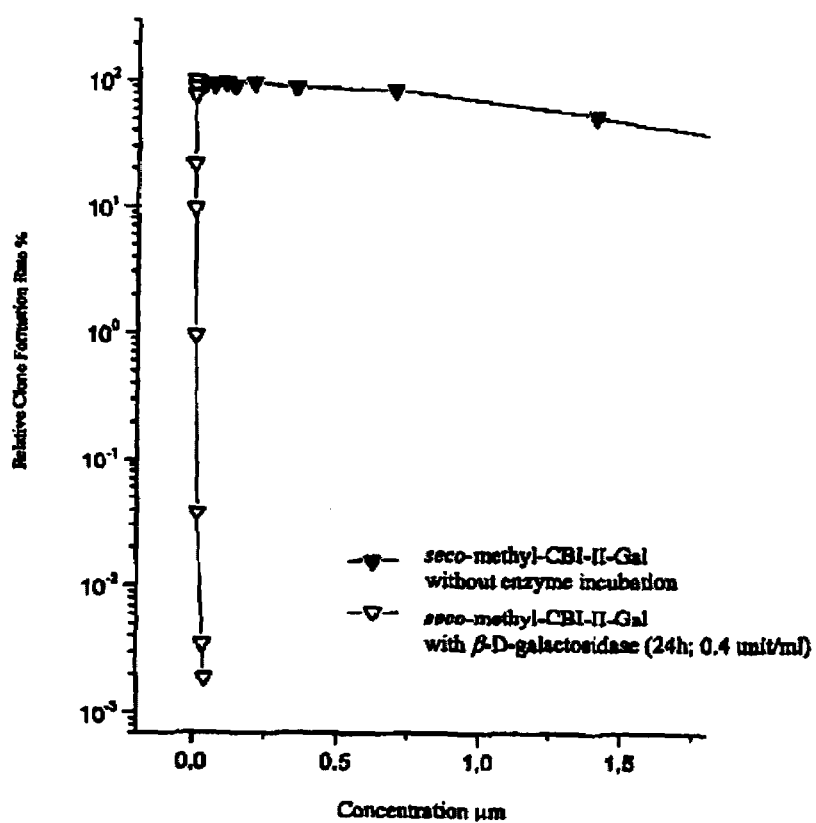
FIG. 1 is a graph showing the antiproliferation action of seco-Methyl-CBI-II-Gal derivatives, with and without β-D-galactosidase, on human bronchial carcinoma cells of line A549.

Within the scope of the present invention a hydroxy protective group generally denotes a protective group from the following list: tert.-butoxydiphenylsilyl, trimethylsilyl, triethylsilyl, triisopropylsilyl, tert.-butyldimethylsilyl, tert.-butyldiphenylsilyl, triphenylsilyl, tri-methylsilylethoxycarbonyl, benzyl, benzyloxycarbonyl, 2-nitrobenzyl, 4-nitrobenzyl, 2-nitrobenzyloxycarbonyl, 4-nitrobenzyloxycarbonyl, tert.-butyloxycarbonyl, allyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methylthiomethyl, methoxyethoxymethyl, [2-(trimethylsilyl)ethoxy]methyl, 2-(methylthiomethoxy)ethoxycarbonyl, benzoyl, 4-methylbenzoyl, 4-nitrobenzoyl, 4-fluorobenzoyl, 4-chlorobenzoyl or 4-methoxybenzoyl. Acetyl, benzoyl, benzyl or methylbenzyl are preferred.

Amino-protective groups within the scope of the present invention are the conventional amino-protective groups used in peptide chemistry. These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert.-butoxycarbonyl, allyloxycarbonyl, vinyloxycarbonyl, 2-nitrobenzyloxycarbonyl, 3,4,5-trimethoxybenzyloxycarbonyl, cyclohexoxycarbonyl, 1,1-dimethylethoxycarbonyl, adamantylcarbonyl, phthaloyl, 2,2,2-trichloroethoxycarbonyl, 2,2,2-trichlorotertbutoxycarbonyl, menthyloxycarbonyl, phenoxycarbonyl, 4-nitrophenoxycarbonyl, fluoroenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl or 4-nitrophenyl. Benzyloxycarbonyl, tert.-butoxycarbonyl and acetyl are preferred.

The process according to the invention for the production of the new compounds of the general formulae (I), (II), (III), (IV), (V) and (VI) according to claim 4 may be illustrated by way of example by the following reaction scheme:

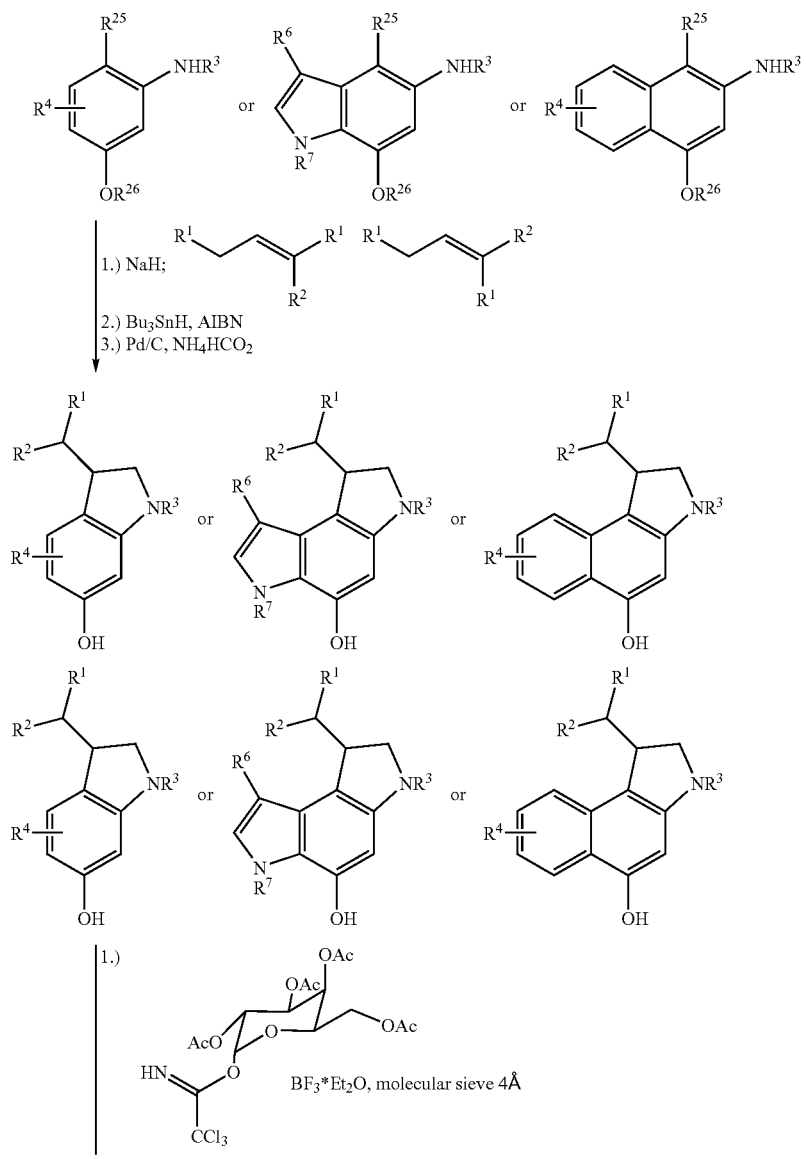

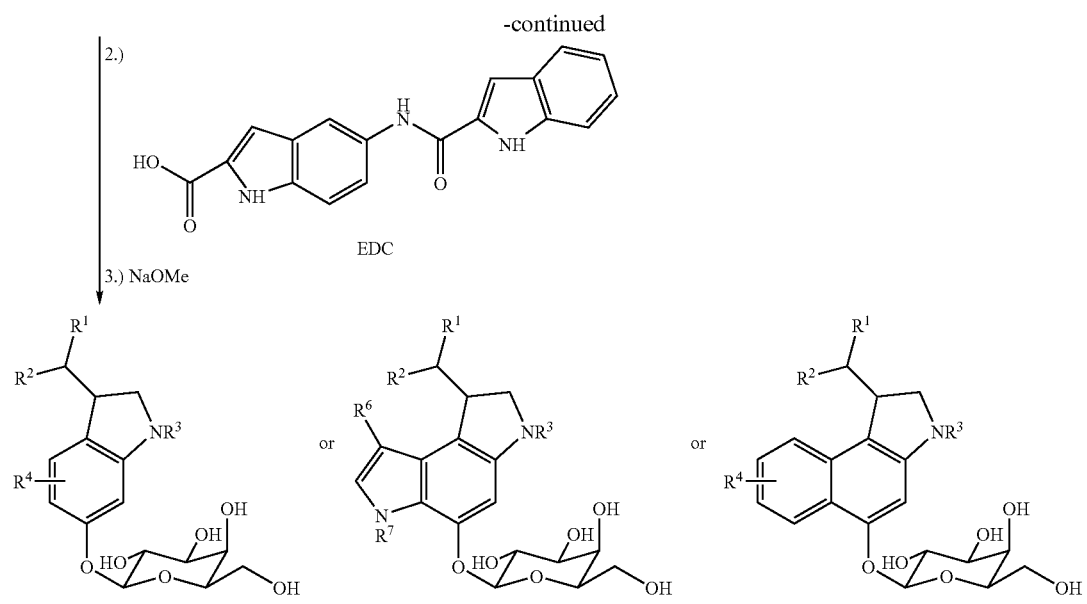
The process according to the invention for the production of the new compounds of the general formula (VII) may be illustrated by way of example by the following reaction scheme:
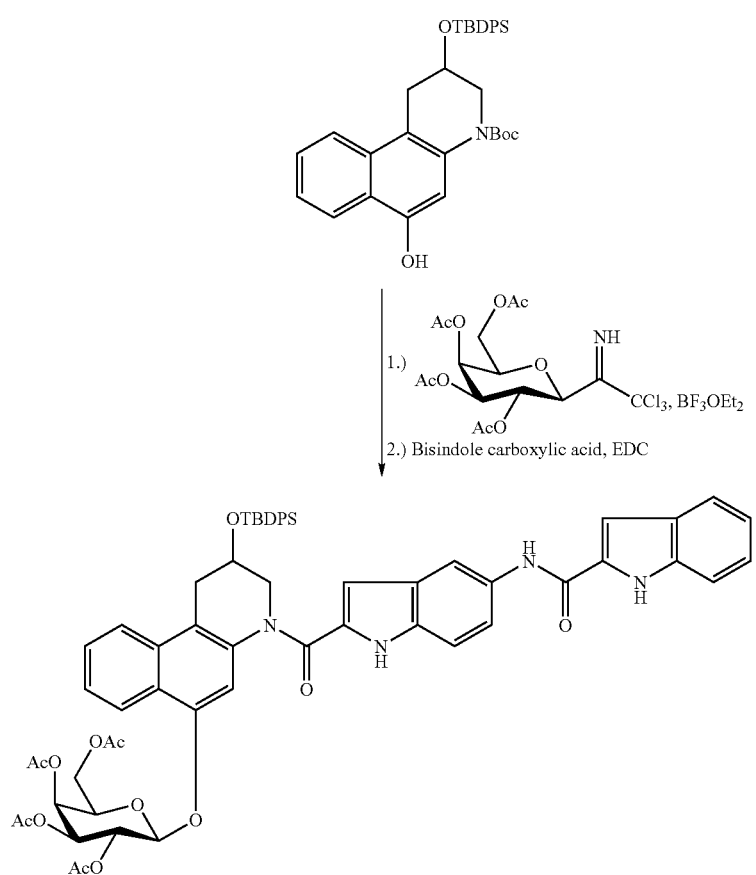

-continued

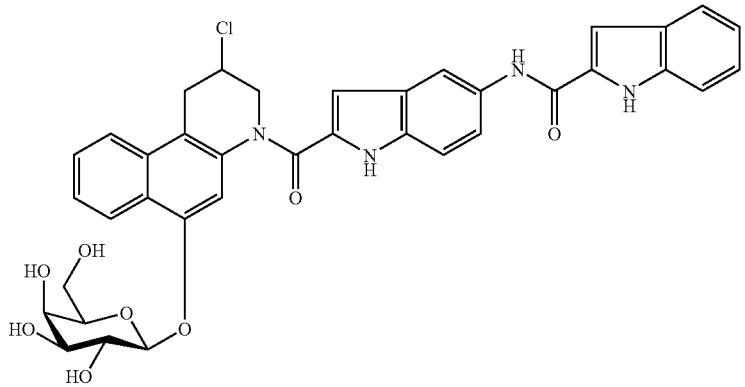

Suitable bases for the deprotonation within the meaning given above are alkali metal and alkaline earth metal hydrides, preferably sodium hydride. Aprotic organic solvents are suitable as solvents, for example dimethylformamide, tetrahydrofuran or diethyl ether. Dimethylformamide is preferred. The reaction is carried out in a temperature range from −30° C. to 80° C. under normal pressure, preferably at 0° C. to 80° C.

Cyclisation is carried out at normal pressure under an argon atmosphere in a temperature range from 50° C. to 110° C., preferably at 80° C. to 110° C., in the presence of tributyltin hydride. Suitable solvents are aromatic hydrocarbons, preferably benzene and toluene. α,α'-azo-isobutyronitrile is preferred as free-radical initiator.

The splitting off of the protective groups on the phenolic oxygen is carried out by hydrogenolytic splitting, in the case of the benzyl group in the presence of a catalyst, for example a mixture of palladium/C and palladium/CaCO$_3$, with hydrogen or by addition of ammonium formate, in one of the solvents listed above, preferably tetrahydrofuran, methanol or acetone, in a temperature range from 0° C. to 60° C., preferably at 20° C. to 50° C., or by lithium or sodium in liquid ammonia.

To produce the glycosidised prodrugs, the free phenol is coupled with a glycosyl donor. The donor may be selected from glycosyl halides, glycosyl tricholoroacetimidates or other suitable compounds.

Suitable promoters for the glycosidation are in general silver, mercury and ammonium salts or Lewis acids, such as for example boron trifluoride/ethyl etherate, trimethysilyl-trifluoromethane-sulfonate, boron tribromide or aluminium trichloride, and in the case of amide coupling, carbodiimides such as for example N,N'-dicyclohexylcarbodiimide (DCC) or N-(3-dimethylaminopropyl)-N'-ethylcarbodiimide hydrochloride (EDC). Boron trifluoride ethyl etherate and EDC are preferred.

Suitable promoters for the conversion with enol ethers are in general substituted arylsulfonic acids such as for example naphthylsulfonic acid, p-toluenesulfonic acid (PTS) or pyridinium-p-toluenesulfonate (PPTS); PPTS and PTS are preferred.

Suitable solvents are organic solvents that ensure the solubility of the respective promoter. Suitable solvents include in general halogenated hydrocarbons such as methylene chloride, chloroform or carbon tetrachloride, or ethers such as for example diethyl ether, tetrahydrofuran and dioxane, as well as dimethyl sulfoxide or dimethylformamide.

In the case of the promoter boron triflouride/ethyl etherate it is preferred to use methylene chloride and chloroform, and in the case of EDC it is preferred to use dimethylformamide and dimethyl sulfoxide.

The promoter is used in an amount of 0.2 mole to 10.0 moles, preferably 3.0 moles to 8.0 moles, referred to 1 mole of the compound of the general formulae (I), (II) or (III).

The conversion is generally carried out at normal pressure under an inert gas atmosphere. It is however also possible to carry out the process under excess pressure or under reduced pressure (for example in a range from 0.5 to 5 bar).

The process according to the invention is generally carried out in a temperature range from −30° C. to +100° C.

Among derivatisations, deacetylations are carried out in order to split off the protective groups on the sugar.

The splitting off of the protective groups on the sugar radical is carried out by a conventional method in inert solvents in the presence of a base, or by hydrogenolysis.

Suitable bases for the splitting off are conventional inorganic bases. These preferably include alkali hydroxides or alkaline earth hydroxides such as for example sodium hydroxide, potassium hydroxide or barium hydroxide, or alkali carbonates such as sodium or potassium carbonate or sodium hydrogen carbonate, or alkali alcoholates such as sodium ethanolate, sodium methanolate, potassium ethanolate, potassium methanolate or potassium tert.-butanolate. Sodium methanolate or potassium methanolate are particularly preferably used.

Suitable solvents for the splitting off are the conventional organic solvents used for a saponification. These preferably include alcohols such as methanol, ethanol, propanol, isopropanol or butanol, or ethers such as tetrahydrofuran or dioxane, or dimethylformamide or dimethyl sulfoxide. Alcohols such as methanol, ethanol, propanol or isopropanol are particularly preferably used. It is also possible to use mixtures of the aforementioned solvents.

The splitting off is generally carried out in a temperature range from 0° C. to +100° C., preferably from +20° C. to +60° C. In general the splitting off is carried out under normal pressure. It is however also possible to operate under reduced pressure or under excess pressure (for example from 0.5 to 5 bar).

The splitting off of special hydroxy protective groups (silyl groups and benzyl groups) is performed for example with tetrabutylammonium fluoride or other fluoride compounds and/or by hydrogenolytic splitting, in the case of the benzyl group in the presence of a catalyst, for example a mixture of palladium/C and palladium/CaCO$_3$, with hydrogen, or by addition of ammonium formate, in one of the solvents listed above, preferably tetrahydrofuran, methanol or acetone, in a temperature range from 0° C. to 60° C., preferably at 20° C. to 50° C., or by lithium or sodium in liquid ammonia.

The splitting off of the amino protective groups is generally also carried out according to known methods, for example with Lewis acids in dichloromethane.

The compounds of the general formulae (IX), (X) (XI), (XII), (XIII) (XX) and (XXI) are known per se and may be produced by methods described in the literature.

The compounds of the general formulae (XIV), (XV), (XVI), (XVII), (XVIII) and (XIX) are novel and may be produced by the processes described above.

The glycosides of 6-hydroxy-2,3-dihydro-1H-indoles of the general formula (IV), the glycosides of 5-hydroxy-1,2-dihydro-3H-pyrrolo[3,2-e]indoles (V), the glycosides of 5-hydroxy-1,2-dihydro-3H-benzo[e]indoles (VI) and the glycosides of 6-hydroxy-1,2,3,4-tetrahydrobenzo[f]-quinolines of the general formula (VII) as well as acetals of the 6-hydroxy-1,2,3,4-tetrahydrobenzo[f]-quinolines of the general formula (VIII) constitute a largely non-toxic transport form for these highly cytocidal compounds. By using glycohydrolases that are preferably coupled to tumour-specific monoclonal antibodies, and in the case of (VIII) by H$^+$, the largely non-toxic transport forms are converted into the highly cytocidal 6-hydroxy-2,3-dihydro-1H-indole or 5-hydroxy-1,2-dihydro-3H-pyrrolo[3,2-e]indole or 5-hydroxy-1,2-dihydro-3H-benzo[e]indole derivatives or 6-hydroxy-1,2,3,4-tetrahydro-benzo[f]-quinolines with free phenolic hydroxy groups. In this way it is possible, using a largely non-toxic compound, selectively to release a cytocidal compound in the tumour, the concentration of the cytocidal compound in the normal tissue being low. The dose-limiting side effects of the toxic 6-hydroxy-2,3-dihydro-1H-indole or 5-hydroxy-1,2-dihydro-3H-pyrrolo[3,2-e] indole or 5-hydroxy-1,2-dihydro-3H-benzo[e]indole derivates or 6-hydroxy-1,2,3,4-tetrahydrobenzo[f]-quinolines can be reduced in this way.

Investigations of the Cytotoxicity

Cell Line: A 549

Substances: [3-((5'-(((1H-indol-2''-yl)-carbonyl)-amino)-1H-indol-2'-yl)carbonyl)-1-(1'-chloroethyl)-1,2-dihydro-3H-benz-[e]indol-5-yl]-β-D-galactopyranoside (seco-methyl-CBI-II-Gal) and 2-chloro-4-[5'-(((1H-indol-2''-yl)-carbonyl)-amino)-1H-indol-2'-yl)carbonyl]-1,2,3,4-tetrahydrobenzo[f]quinolin-6-yl}-β-D-galactopyranoside (7, seco-CBC-II-Gal)

Cell culture: The cultivation of the cell line A 549 (ATCC no. CCL 185) in the form of monolayer cultures was carried out at 37° C. and 7.5% CO$_2$ in air in DMEM (Dulbecco's Modified Eagle's Medium from Biochrom, order no. TO43-10), that had been supplemented with 10% foetal calf serum (from Gibco).

Toxin exposure: The compounds were freshly dissolved with DMSO (Merck, order no. 2950.0500) before the experiment.

The toxin dilutions were carried out for pH 7.4 in DMEM. The pH value of the culture medium had previously been adjusted with 0.1 N HCl, taking into account the pH fluctuations due to the CO$_2$ gassing. After the cells had been added in concentrations of 10$^2$, 10$^3$, 10$^4$ and 10$^5$ to 6-well tissue culture plates (Becton Dickinson, order no. 3046) and cultivated until adherence occurred, the culture was exposed to the toxin for 24 hours in each case once with and once without the addition of 0.4 unit/ml of β-D-galactosidase. Fresh culture medium, pH 7.4, was then added to the cells, which were cultivated for 12 days until the formation of macroscopically observable colonies. The colonies were fixed, stained with Löffler's Methylene Blue (Merck, order no. 1287) and counted.

Figure 2:
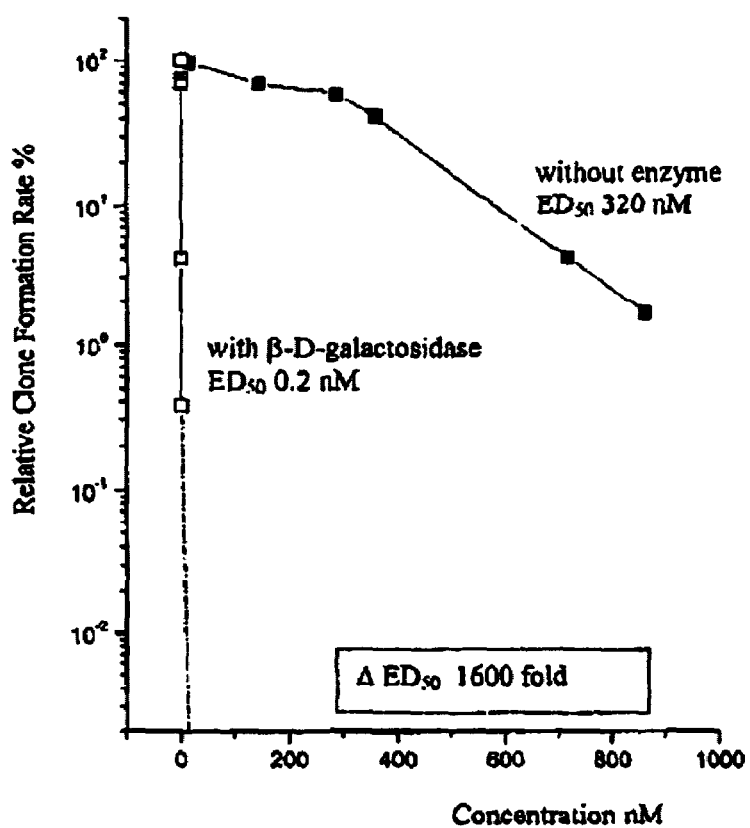
FIG. 2 is a graph showing the antiproliferation action of seco-CBC-II-Gal derivatives, with and without β-D-galactaaidase, on human bronchial carcinoma cells of line A549.

FIG. 1 and FIG. 2 show the results of the antiproliferation action of two inventive compounds on human bronchial carcinoma cells of lane A549. The results of the antiproliferation testing for seco-Methyl-CBI-II-Gal derivatives both with and without β-D-galactosidase, are shown in FIG. 1. The results of the antiproliferation testing for seco-CBC-Il-Gal derivatives both with and without β-D-galactosidase, are shown in FIG. 2.

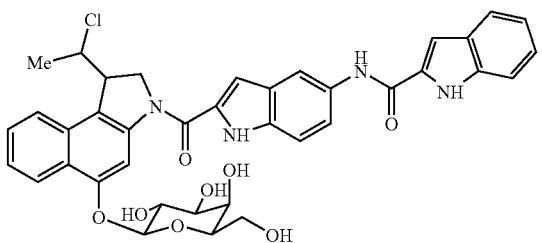

seco-Methyl-CBI-II-Gal

Antiproliferative Action of Seco-methyl-CBI-II Deratives on Human Bronchial Carcinoma Cells of Line A549

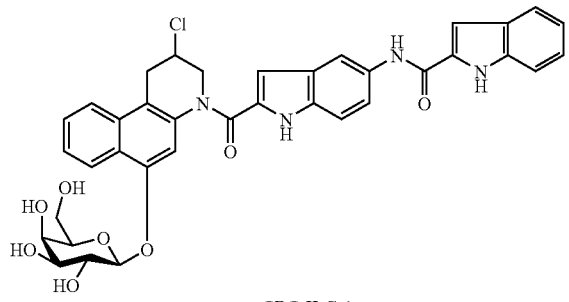

seco-CBC-II-Gal

Antiproliferative Action of Seco-CBC-II-Gal Deratives on Human Bronchial Carcinoma Cells of Line A549

The present invention includes pharmaceutical preparations that contain, in addition to non-toxic, inert, pharmaceutically suitable carriers, also one or more compounds of the formulae (I), (II), (III), (IV), (V) and/or (VI), or which consist of one or more active substances of the formulae (I), (II), (III), (IV), (V) and/or (VI), (VII), (VIII), as well as processes for the production of these preparations.

The active substances of the formulae (I), (II), (III), (IV), (V) and/or (VI) should be present in the pharmaceutical preparations listed above in a concentration of about 0.1 to 99.5 wt. %, preferably about 0.5 to 95 wt. % of the total mixture.

The pharmaceutical preparations listed above may contain, apart from the compounds of the formulae (I), (II), (III), (IV), (V) and/or (VI), (VII), (VIII), also further pharmaceutical active substances.

The production of the pharmaceutical preparations listed above is carried out in a conventional way by known methods, for example by mixing the active substance or substances with the carrier or carriers.

In general it has proved advantageous in both human medicine and in veterinary medicine to administer the active substance or substances according to the invention in total amounts of about 0.5 to about 500, preferably 1 to 150 mg/kg body weight per 24 hours, optionally in the form of several individual doses, in order to achieve the desired results. An individual dose contains the active substance or substances preferably in amounts of about 1 to about 100, in particular 1 to 80 mg/kg body weight. It may however be necessary to deviate from the aforementioned dosages, and more specifically depending on the type and body weight of the subject to be treated, the nature and severity of the disease, the nature of the preparation and application of the medicament, as well as the period or time interval within which the administration takes place.

Experimental Part

1. General Methods

Conversions were carried out where necessary in heated glass apparatus under a slight argon excess pressure. The solvents were dried and distilled corresponding to conventional laboratory procedures. Commercial products were used as a rule without further purification.

1.1 Equipment Used

Melting points: melting point determination apparatus FP61 from Mettler. The values are uncorrected.

Infrared spectra: Model IFS 25 from Bruker. Crystalline substances were measured as KBr pellets, and non-crystalline compounds as a film between KBr plates. Polystyrene bands at 1601 cm$^{-1}$ served for purposes of calibration.

UV/VIS spectra: Models Lambda 2 and Lambda 9 from Perkin-Elmer.

$^1$H-NMR spectra: Model AMX-300 (300 MHz) from Bruker and Model VXR-500 (500 MHz) from Varian. The chemical shifts are given in δ-scale units. Tetramethylsilane ($δ_{TMS}$=0.00 ppm) served as internal standard. The following abbreviations are used to characterise the multiplicities of the signals: s (singlet), d (doublet), t (triplet), m (multiplet), $m_c$ (centred multiplet), br (broad signal). The spectra were as a rule interpreted corresponding to first order. The coupling constants J are given in Hertz (Hz).

$^{13}$C-NMR spectra: Model XL-200, VXR-200 (50.3 MHz), VXR-500 (125 MHz) from Varian, Model AMX-300 (75.5 MHz) from Bruker. Tetramethylsilane or the specified solvent served as internal standard. The chemical shifts are determined from the $^1$H broadband-decoupled spectra, and the signal multiplicities were determined in multiplet-selection experiments (APT pulse sequence).

Mass spectra: Model MAT 311A (low resolution spectra) and MAT 731 (high resolution spectra) from Varian. The relative intensities are given in brackets referred to the base peak (I=100).

Elementary analyses: Hambloch Microanalytical Laboratory developed by the Institute for Organic Chemistry, University of Göttingen.

1.2 Chromatographic Methods

Thin layer chromatography (TC): SIL G/UV$_{254}$ precoated TC sheets from Machery, Nagel & Co. (layer thickness 0.25 mm) were used. $R_f$ values are given (solvent height relative to the solvent front). The following abbreviations are employed for the solvents that are used: EA (ethyl acetate), PE (petroleum ether in the boiling point range 40–75° C.), CH$_2$Cl$_2$ (dichloromethane). In addition to the UV detection, a vanillin-sulfuric acid solution (0.5 g vanillin, 3 ml sulfuric acid, 85 ml methanol and 10 ml acetic acid) served as staining reagent.

Column filtration (CF) and column chromatography (CC): all column chromatography-separations were carried out with silica gel 60 (grain size: 0.063–0.200 mm) from Machery, Nagel & Co. or with silica gel 60 (grain size: 0.200–0.400 mm). A substance/absorbent ratio of between 50:1 and 200:1 was used depending on the separation task.

Explanation of the Abbreviations Used in the Experimental Part:

| | |
|---|---|
| PE = | Petrol ether |
| EtOAc = | Ethyl acetate |
| DMF = | Dimethylformamide |
| EDC = | N-(3-dimethylaminopropyl)-N'-ethylcarbodiimide hydrochloride |
| AIBN = | α, α'-azoisobutyronitrile |

PRODUCTION EXAMPLE

Example 1

2-amino-4-benzyloxy-N-[E/Z-1'-(3'-chloro)-but-2'-enyl]-N-(tert.-butoxycarbonyl)-1-iodonaphthalene

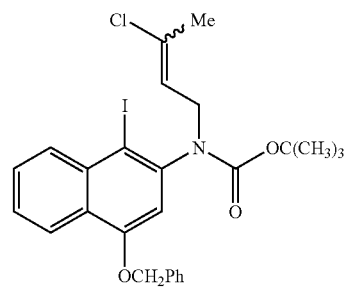

400 mg (10.0 mmoles) of sodium hydride in the form of a 60% suspension in paraffin oil were added to a solution of 2.00 g (4.21 mmoles) of 2-amino-4-benzyloxy-N-(tert.-butoxycarbonyl)-1-iodonaphthalene [produced for example according to D. L. Boger, J. A. McKie, J. Org. Chem. 1995, 60, 1271] in 50.0 ml of dry DMF. The reaction mixture was stirred for 45 minutes at room temperature and 1.20 ml (1.37 g, 10.9 mmoles) of an isomeric mixture of E/Z-1,3-dichlorobut-2-ene were added dropwise. The reaction mixture was then stirred for 3 hours at room temperature. After hydrolysis with saturated NH$_4$Cl solution extraction was carried out three times with EtOAc. The combined organic phases were washed five times with water and then once with saturated NaCl solution and dried over Na$_2$SO$_4$. The solvents were removed in vacuo; a column chromatography purification of the residue (100 g silica gel, 40–63 μm, solvent PE/EtOAc 10:1) yielded 2.32 g (4.11 mmoles, 98% yield) of the target compound as a slightly yellowish oil.

R$_f$=0.40 (E) and 0.33 (Z) (PE/EtOAc 10:1)

Example 2

5-benzyloxy-3-(tert.-butoxycarbonyl)-1-(1'-chloroethyl)-1,2-dihydro-3H-benzo[e]indole

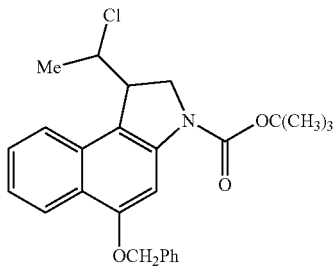

573 mg (1.02 mmoles) of the compound from Example 1 were dissolved in 18 ml of dry, degassed toluene and 0.35 ml (384 mg, 1.32 mmoles) of tributyltin hydride and 42.0 mg (255 μmoles) of AIBN were added thereto. The mixture was heated to 80° C. and stirred for 3.5 hours at this temperature. The residue obtained after concentration by evaporation was taken up in diethyl ether and washed with the same volume of a 10% aqueous solution of KF. The residue obtained after drying the organic phase over Na$_2$SO$_4$ and removal of the solvents was subjected to a column chromatography purification (100 g silica gel, 40–63 μm, solvent PE/EtOAc 20:1). 187 mg (419 μmoles, 42% yield) of the syndiastereomer and 180 mg (411 μmoles, 41% yield) of the antidiastereomer of the target compound were obtained.

R$_f$=0.52 (syn) and 0.32 (anti) (PE/EtOAc 10:1)

Example 3 syn-3-(tert.-butoxycarbonyl)-1-(1'-chloroethyl)-5-hydroxy-1,2-dihydro-3H-benzo[e]indole

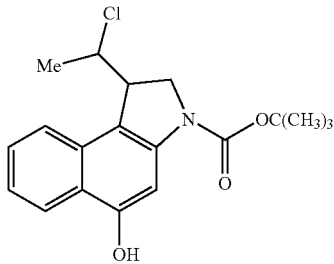

354 mg (808 μmoles) of the syn-isomer of the compound from Example 2 were dissolved in 17.0 ml of acetone and 389 mg (366 μmoles) of 10% Pd on activated charcoal as well as 318 mg (5.05 mmoles) of ammonium formate were added thereto. The reaction mixture was stirred for 2 hours at 50° C. The reaction solution was filtered through celite that had been thoroughly washed with EtOAc. The residue obtained after concentrating the filtrate by evaporation was purified by column chromatography on silica gel (40 g, 40–63 μm, solvent PE/EtOAc 5:1) and thereby yielded 111 mg (320 μmoles, 85% yield) of the target compound.

R$_f$=0.48 (PE/EtOAc 5:1)

Example 4 syn-[3-((5'-(((1H-indol-2''-yl)carbonyl)amino)-1H-indol-2'-yl)carbonyl)-1-(1'-chloroethyl)-1,2-dihydro-3H-benzo[e]indol-5-yl]-2,3,4,6-tetra-O-acetyl-β-D-galactopyranoside

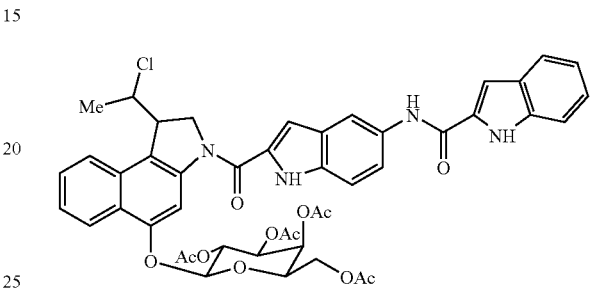

50.0 mg (144 μmoles) of the compound from Example 3 were dissolved in 7.0 ml of dry dichloromethane. 1.00 g of thoroughly heated molecular sieve (4Å) as well as 74.0 mg (148 μmoles) of O-(2,3,4,6-tetra-O-acetyl-α-D-galactopyranosyl)-trichloroacetimidate were added thereto. The reaction mixture was stirred for 30 minutes at room temperature, following which 59.0 μl (66.7 mg, 470 μmoles) of boron trifluoride ethyl etherate were added slowly at −10° C. The reaction mixture was stirred for a further 1 hour at −10° C., and then for 4 hours at room temperature. The mixture was concentrated by evaporation to dryness under a high vacuum and then suspended under an argon atmosphere in 2.5 ml of dry, degassed DMF. 40.9 mg (128 μmoles) of 5-[((1H-indol-2'-yl)carbonyl)amino]-1H-indole-2-carboxylic acid as well as 62.0 mg (320 μmoles) of EDC were added and the whole was stirred for 36 hours at room temperature. The mixture was concentrated by evaporation to dryness and the residue was subjected to column chromatography on silica gel (50 g, 40–63 μm, solvent 33–66% EtOAc in PE). 69.5 mg (79.0 μmoles, 55% yield) of the target compound were obtained.

R$_f$=0.58 (PE/acetone/methanol 10:6:1)

Example 5 syn-[3-((5'-(((1H-indol-2''-yl)carbonyl)amino)-1H-indol-2'-yl)carbonyl)-1-(1'-chloroethyl)-1,2-dihydro-3H-benzo[e]indol-5-yl]-β-D-galactopyranoside

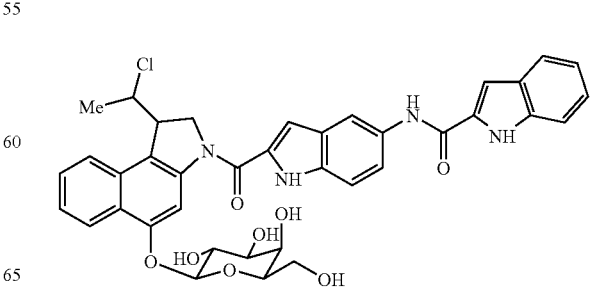

64.0 mg (72.5 μmoles) of the compound from Example 4 were dissolved in 2.0 ml of dry methanol and 9.0 μl (48.6 μmoles) of a 5.4 M solution of sodium methanolate in methanol were added. After stirring for 3 hours at room temperature 0.5 ml of water was added and the precipitate was filtered off. 19.2 mg (27.0 μmoles, 37% yield) of the target compound were obtained.

Example 6

Alcohol 1 is known in the literature (D. L. Boger, J. A. McKie, C. W. Boyce, *Synlett* 1997, 515–517) and was obtained in a slightly modified synthesis sequence according to conventional laboratory procedures.

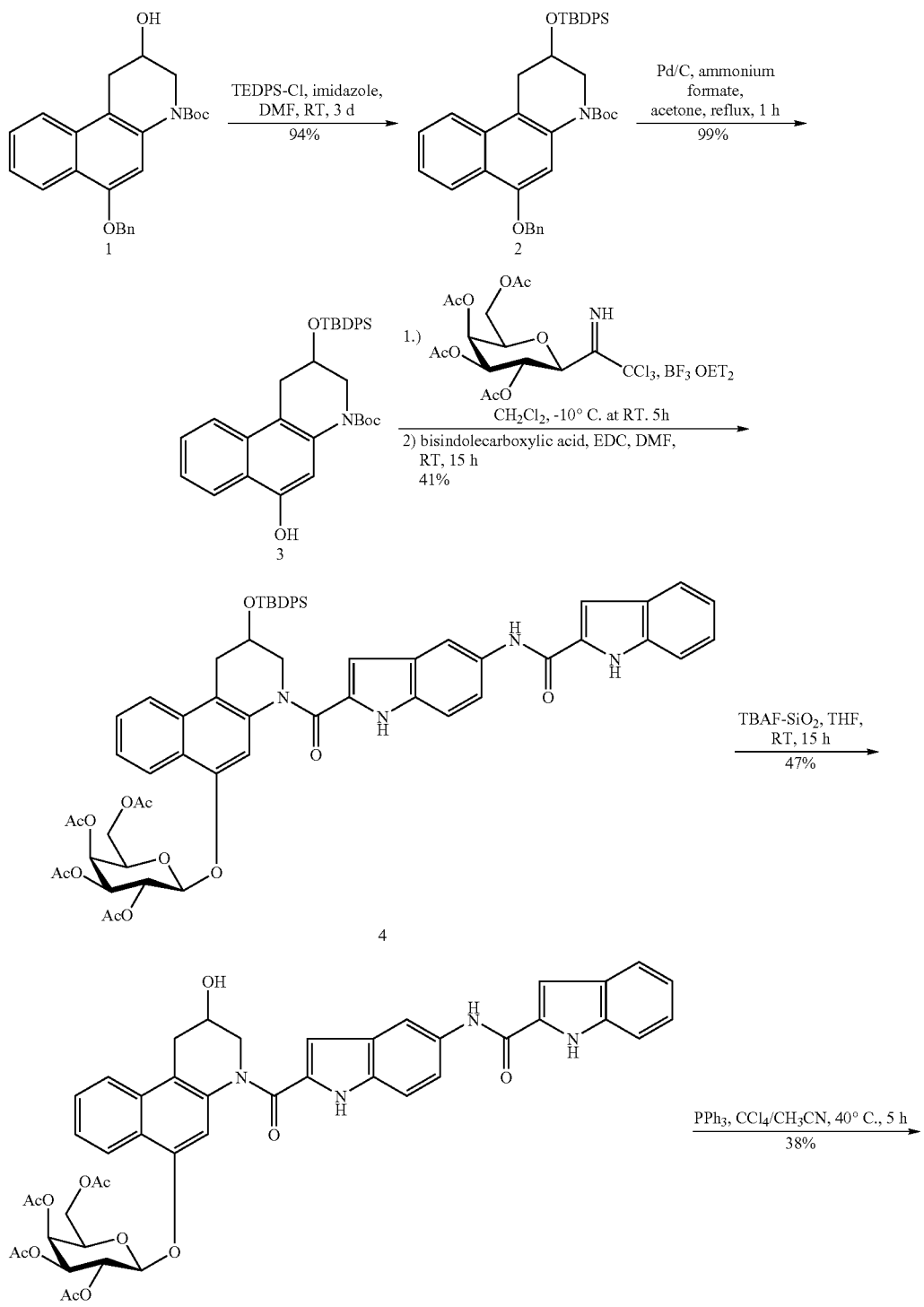

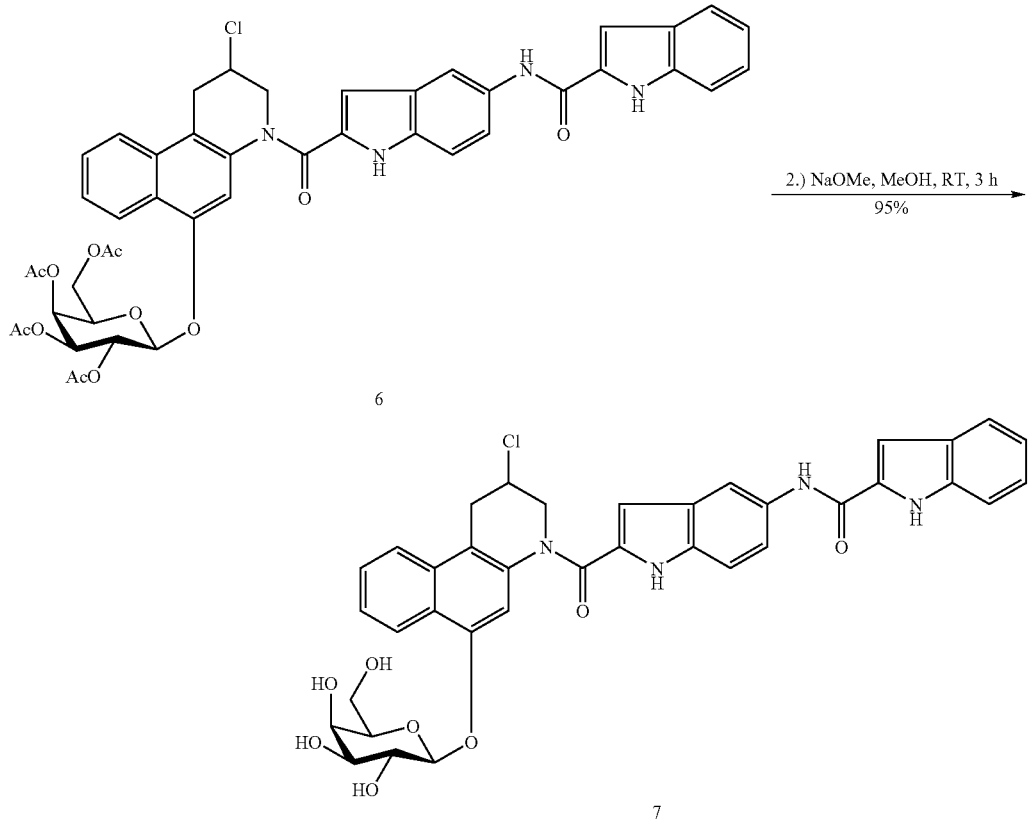

6-benzyloxy-2-(tert-butyldiphenylsilanyloxy)-N-(tert-butoxycarbonyl)-2,3-dihydro-1H-benzo[f]quinoline (2)

A solution of the alcohol 1 in absolute DMF (5 ml) was added to a mixture of imidazole (1.47 g, 21.6 mmoles, 5 equivs.) and tert-butyldiphenylsilyl chloride (2.21 ml, 2.37 g, 8.63 mmoles, 2 equivs.) and the reaction mixture was stirred for three days at room temperature. The reaction mixture was worked up by adding the yellow solution to iced water and was extracted twice with $CH_2Cl_2$ and once with $Et_2O$. The combined organic phases were washed three times with saturated citric acid solution and then with saturated NaCl solution, dried over $MgSO_4$, and the solvent was removed in vacuo. The oily yellow crude product thus obtained yielded after column chromatography purification (PE/EE=30:1) 2.60 g (94%) of the silyl ether 2 in the form of a white solid foam.

$R_f$=0.59 (PE/EE=3:1), brown (VSS);

UV ($CH_3CN$): $\lambda_{max}$(lg $\epsilon$)=253 nm (3.859), 303 (3.089)

IR (KBr): ñ=3070 $cm^{-1}$ (Ar—H), 2930 (CH), 1702 (C═O), 1595, 1367, 1254, 1158, 757.

$^1$H-NMR (300 MHz, $CDCl_3$): δ=1.08 (s, 9 H, SiC($CH_3$)$_3$), 1.46 (s, 9 H, OC($CH_3$)$_3$), 2.90 (dd, J=17.0, 6.4 Hz, 1 H, 1-$H_a$), 3.05 (dd, J=17.0, 6.0 Hz, 1 H, 1-$H_b$), 3.62 (dd, J=12.5, 8.3, Hz, 1 H, 3-$H_a$), 4.00 (dd, J=12.5, 3.0 Hz, 1 H, 3-$H_b$), 4.29 (dddd, J=8.3, 6.4, 6.0, 3.0 Hz, 1 H, 2-H), 5.19 (s, 2 H, $CH_2$Ph), 7.22 (s, 1 H, 5-H), 7.32–7.48 (m, 11 H, 5×Bn-H, 4×Ph-$H_m$, 2×Ph-$H_p$), 7.52–7.54 (m, 2 H, 8-H, 9-H), 7.59 (d, J=8.3 Hz, 1 H, 10-H), 7.70–7.75 (m, 4 H, 4×Ph-$H_o$), 8.29 (dd, J=8.3, 1.1 Hz, 1 H, 7-H).

$^{13}$C-NMR (50 MHz, $CDCl_3$): δ=19.22 (Si$C$($CH_3$)$_3$), 26.98 (SiC($CH_3$)$_3$), 28.39 (OC($CH_3$)$_3$), 33.76 (C-1), 50.24 (C-3), 66.69 (C-2), 70.10 ($CH_2$Ph), 80.93 (O$C$($CH_3$)$_3$), 103.8 (C-5), 113.7 (C-10b), 122.3, 122.4, 124.1 (C-7, C-10, C-8), 123.4 (C-6a), 127.8 (C-9), 127.6 (2×Bn-$C_o$), 127.7 (4×Ph-$C_m$), 127.9 (Ph-$C_p$), 128.5 (2×Bn-$C_m$), 129.8 (2×Ph-$C_p$), 132.6 (C-10a), 133.7, 134.0 (2×Ph-$C_i$), 135.7 (4×Ph-$C_o$), 135.8 (Bn-$C_i$), 137.1 (C-4a), 152.3 (C═O), 154.9 (C-6).

MS (DCI, $NH_3$): m/z (%)=661 (70) [M+$NH_4$]$^+$, 644 (12) [M+H]$^+$, 605 (22) 274 (100).

| $C_{25}H_{27}NO_4$ (387.47). | calc.: | C: 76.48 | H: 7.05 | N: 2.18 |
|---|---|---|---|---|
| | found: | C: 76.35 | H: 7.29 | N: 2.12 |

2-(tert-butyldiphenylsilanyloxy)-6-hydroxy-4-(tert-butoxycarbonyl)-2,3-dihydro-1H-benzo[f]quinoline (3)

Ammonium formate (1.65 g, 26.3 mmoles, 6.5 equivs.) and 10% Pd on activated charcoal (2.15 g, 2.02 mmoles, 0.5 equiv.) were added to a solution of the benzyl ether 2 (2.60 g, 4.04 mmoles) in acetone (100 ml) and refluxed for one hour. After cooling to room temperature the catalyst was filtered off through celite and thoroughly rewashed with acetone. After removing the solvent in vacuo and column filtration (PE/EE=5:1) 2.22 g (99%) of a white foam were obtained.

Mp.: 71–73° C.

$R_f$=0.40 (PE/EE=5:1), yellow (VSS);

UV (CH$_3$CN): $\lambda_{max}$ (lg ϵ)=253 nm (3.842), 299 (2.986), 271 (2.777).

IR (KBr): ñ=3372 cm$^{-1}$ (OH), 3070 (Ar—H), 2931(CH), 1675 (C=O), 1597, 1368, 1256, 1156, 758.

$^1$H-NMR (300 MHz, CDCl$_3$): δ=1.03 (s, 9 H, SiC(CH$_3$)$_3$), 1.37 (s, 9 H, OC(CH$_3$)$_3$), 2.83 (dd, J=16.6, 6.8 Hz, 1 H, 1-H$_a$), 2.99 (dd, J=16.6, 6.4 Hz, 1 H, 1-H$_b$), 3.49 (dd, J=12.4, 8.3 Hz, 1 H, 3-H$_a$), 3.94 (dd, J=12.4, 3.4 Hz, 1 H, 3-H$_b$), 4.29 (dddd, J=8.3, 6.8, 6.4, 3.4 Hz, 1 H, 2-H), 7.01 (s$_{br}$, 1 H, 6-OH), 7.14–7.39 (m, 9 H, 5-H, 8-H, 9-H, 4×Ph-H$_m$, 2×Ph-H$_p$), 7.46 (d, J=8.3 Hz, 1 H, 10-H), 7.62–7.67 (m, 4 H, Ph-H$_o$), 7.97 (d, J=7.5 Hz, 1 H, 7-H).

$^{13}$C-NMR (50 MHz, CDCl$_3$): δ=19.26 (SiC(CH$_3$)$_3$), 27.00 (SiC(CH$_3$)$_3$), 28.27 (OC(CH$_3$)$_3$), 33.71 (C-1), 50.40 (C-3), 66.69 (C-2), 81.37 (OC(CH$_3$)$_3$), 105.7 (C-5), 112.9 (C-10b), 122.2, 122.5, 123.7 (C-7, C-10, C-8), 122.7 (C-6a), 126.5 (C-9), 127.7 (4×Ph-C$_m$), 129.8 (2×Ph-C$_p$), 132.7 (C-10a), 133.8, 134.0 (2×Ph-C$_i$), 135.4 (C-4a), 135.7 (4×Ph-C$_o$), 150.4 (C=O), 154.3 (C-6).

MS (DCI, NH$_3$): m/z (%)=571 (100) [M+NH$_4$]$^+$.

| C$_{34}$H$_{39}$NO$_4$Si (553.76). | calc.: | C: 73.74 | H: 7.10 |
|---|---|---|---|
| | found: | C: 73.53 | H: 7.32 |

{4-[5'-((1H-indole-2"-carbonyl)-amino)-1H-indole-2'-carbonyl]-2-(tert-butyldiphenylsilanyloxy)-1,2,3,4-tetrahydrobenzo[f]quinolin-6-yl}-2*,3*,4*,6*-tetra-O-acetyl-β-D-galactopyranoside (4)

Phenol 3 (500 mg, 903 µmoles) and O-(2,3,4,6-tetra-O-acetyl-α-D-galactopyranosyl)-trichloroacetimidate (490 mg, 993 µmoles, 1.1 equivs.) were dissolved in absolute CH$_2$Cl$_2$ (50 ml), stirred for ca. 30 minutes over a 4 Å molecular sieve and then cooled to −10° C. BF$_3$/OEt$_2$ (56.7 µl, 64.1 mg, 451 µmoles, 0.5 equiv.) was then added dropwise at this temperature, immediately producing a yellow colouration. After stirring for three hours at −10° C. further BF$_3$/OEt$_2$ were added (340 µl, 384 mg, 2.71 mmoles, 3.0 equivs.) and the whole was heated to room temperature. Five hours later the reaction mixture was transferred via a transfer cannula to a second flask and thereby separated from the molecular sieve. The yellow solid remaining after removal of the solvent by recondensation was dried for ca. 1 hour in vacuo and then taken up in absolute DMF (20 ml). After addition of bisindole-carboxylic acid (288 mg, 903 µmoles, 1.0 equiv.) and EDC (519 mg, 2.71 mmoles, 3.0 equivs.) the reaction mixture was stirred for 14 hours at room temperature and the yellow precipitate thereby formed was then filtered off through a small amount of celite (post-rinsing with CH$_2$Cl$_2$). The filtrate was washed with water and saturated NaCl solution, dried over MgSO$_4$, and the solvent was removed in vacuo. After column chromatography purification with PE/EE=3:2, 406 mg (41%) of the desired product (4) were obtained as a yellow solid together with 120 mg (15%) of free amine.

$R_f$=0.14 (PE/EE=3:2), red (VSS);

UV (CH$_3$CN): $\lambda_{max}$ (lg ϵ)=311 nm (3.588).

IR (KBr): ñ=3405 cm$^{-1}$ (NH), 3071 (Ar—H), 2932 (CH), 1753 (C=O), 1620 (C=C), 1597, 1370, 1229, 1078, 745.

$^1$H-NMR (300 MHz, acetone-d$_6$): δ=1.00 (s, 9 H, C(CH$_3$)$_3$), 1.89, 1.95, 2.11 (3×s, 12 H, 4×C(O)CH$_3$), 3.13–3.22 (m, 1 H, 1-H$_a$), 3.29 (dd, J=17.3, 5.3 Hz, 1 H, 1-H$_b$), 3.58–3.69 (m, 1 H, 3-H$_a$), 3.82–4.07 (m, 3 H, 6*-H$_2$, 5*-H), 4.09–4.30 (m, 1 H, 3-H$_b$), 4.51–4.58 (m, 1 H, 2-H), 4.70 (d, J=8.0 Hz, 1 H, 1*-H), 4.87 (dd, J=10.5, 3.4 Hz, 1 H, 3*-H), 5.31 (dd, J=7.5, 3.4 Hz, 1 H, 4*-H), 5.40 (dd, J=10.5, 8.0 Hz, 1 H, 2*-H), 6.68 (s, 1 H, 3'-H), 7.01–7.04 (m, 1 H, 5"-H), 7.06 (s, 1 H, 5-H), 7.18–7.69 (m, 18 H, Ph-H, 3"-H, 4"-H, 6"-H, 7"-H, 6'-H, 7'-H, 8-H, 9-H), 7.80 (dd, J=8.9, 8.9 Hz, 1 H, 10-H), 7.99–8.04 (m, 1 H, 7-H), 8.24 (s, 1 H, 4'-H), 9.46 (s, 1H, 5'-NH), 10.70 (s, 1 H, indole-NH), 10.91 (s, 1H, indole-NH).

$^{13}$C-NMR (50 MHz, acetone-d$_6$): δ=15.56 (C(CH$_3$)$_3$), 20.44 (3×CHOC(O)CH$_3$), 20.70 (CH$_2$OC(O)CH$_3$), 27.30 (C(CH$_3$)$_3$), 33.39 (C-1), 51.56 (C-3), 61.96 (C-6*), 67.20 (C-2), 67.92 (C-4*), 69.01 (C-2*), 71.36 (C-3*), 71.63 (C-5*), 101.3 (C-1*), 103.7 (C-3"), 108.0 (C-3'), 109.2 (C-5), 113.0, 113.1 (C-6', C-7'), 113.9 (C-4'), 116.9 (C-10b), 120.1 (C-5"), 120.9, 125.9, 128.0, 130.6 (C-7, C-10, C-4", C-7"), 122.5, 123.6 (C-8, C-9), 124.6 (C-6a), 124.7 (C-6"), 128.2, 128.7 (C-3'a, C-3"a), 128.5 (4×Ph-C$_m$, 2×Ph-C$_p$), 132.5, 132.9, 133.0, 133.7, 134.1, 134.4 (C-10a, 2×Ph-C$_i$, C-5', C-2', C-2", C-7'a), 136.5 (4×Ph-C$_o$), 136.8, 137.9 (C-7"a, C-4a), 151.7 (C-6), 160.6 (2'-C=O), 164.1 (2"-C=O), 170.2, 170.6, 170.7, 170.9 (4×C(O)—CH$_3$).

MS (DCI, NH$_3$): m/z (%)=1102 (100) [M+NH$_4$]$^+$, 1085 (38) [M+H]$^+$.

| C$_{61}$H$_{60}$N$_4$O$_{13}$Si (1085.23). | calc.: | C: 67.51 | H: 5.57 | N: 5.16 |
|---|---|---|---|---|
| | found: | C: 67.69 | H: 5.45 | N: 5.05 |

4-[5'-((1H-indole-2"-carbonyl)-amino)-1H-indole-2'-carbonyl]-2-hydroxy-1,2,3,4-tetrahydro-benzo[f]quinolin-6-yl}-2*,3*,4*,6*-tetra-O-acetyl-β-D-galactopyranoside (5)

The silyl ether 4 (300 mg, 276 µmoles) was dissolved in absolute THF (10 ml), was added together with TBAF to silica gel (754 mg, 829 µmoles, 3 equivs.) and the whole was stirred for six hours at room temperature. The reaction mixture was worked up by adding three small spatula amounts of silica gel and the solvent was removed in vacuo. The residue was purified by column chromatography with PE/EE=1:1→1:5 and yielded 111 mg (47%) of pure alcohol 5 as a yellowish solid.

$R_f$=0.33 (PE/EE=1:5)

UV (CH$_3$CN): $\lambda_{max}$ (lg ϵ)=214 nm (3.772), 240 (3.638), 310 (3.630).

IR (KBr): ñ=3396 cm$^{-1}$ (NH), 3283 (OH), 3075 (Ar—H), 2932 (CH), 1752 (C=O), 1619 (C=C), 1597, 1370, 1230, 1075, 750.

$^1$H-NMR (300 MHz, acetone-d$_6$): δ=1.88, 1.94, 1.95, 2.10 (4×s, 12 H, 4×C(O)CH$_3$), 3.09 (dd, J=17.0, 6.8 Hz, 1 H, 1-H$_a$), 3.51 (dd, J=17.0, 6.4 Hz, 1 H, 1-H$_b$), 3.62–3.72 (m, 2 H, 5*-H, 3-H$_a$), 3.92–4.03 (m, 2 H, 6*-H$_2$), 4.40 (d, J=8.0 Hz, 1 H, 1*-H), 4.43–4.51 (m, 1 H, 2-H), 4.54 (d, J=4.2 Hz, 1 H, OH), 4.56 (dd, J=14.3, 3.4 Hz, 1 H, 3-H$_b$), 4.72 (dd, J=10.6, 3.4 Hz, 1 H, 3*-H), 5.29 (dd, J=6.8, 3.4 Hz, 1 H, 4*-H), 5.33 (dd, J=10.6, 8.0 Hz, 1 H, 2*-H), 6.73 (d, J=1.1 Hz, 1 H, 3'-H), 6.86 (s, 1 H, 5-H), 7.07 (ddd, J=7.9, 7.9, 1.1 Hz, 1 H, 5"-H), 7.23 (ddd, J=7.9, 7.9, 1.1 Hz, 1 H, 6"-H), 7.30 (s, 1 H, 3"-H), 7.45–7.66 (m, 6 H, 4"-H, 7"-H, 6'-H, 7'-H, 8-H, 9-H), 7.95–8.02 (m, 2 H, 7-H, 10-H), 8.24 (d, J=1.1 Hz, 1 H, 4'-H), 9.38 (s$_{br}$, 1H, 5'-NH), 10.70 (s, 1 H, indole-NH), 10.83 (s, 1H, indole-NH).

$^{13}$C-NMR (75 MHz, acetone-d$_6$): δ=20.53 (3×CHOC(O)CH$_3$), 20.71 (CH$_2$OC(O)CH$_3$), 33.86 (C-1), 51.66 (C-3), 61.99 (C-6*), 65.72 (C-2), 67.89 (C-4*), 69.01 (C-2*), 71.40 (C-3*), 71.59 (C-5*), 101.6 (C-1*), 108.0 (C-3"), 109.1 (C-3'), 113.0 (C-5), 113.1, 113.2 (C-6', C-7'), 113.9 (C-4'), 118.1 (C-10b), 120.1, 120.9, 125.9, 128.1 (C-8, C-9, C-4", C 7"), 120.2 (C-5"), 122.6, 123.9 (C-7, C-10), 124.5 (C-6a), 124.7 (C-6"), 128.7, 128.8 (C-3'a, C-3"a), 132.9, 133.0, 133.1, 133.8, 134.5, 136.8, 137.8 (C-10a, C-5', C-2', C-2", C-7'a, C-7"a, C-4a), 151.9 (C-6), 160.5 (2'-C=O), 163.8 (2"-C=O), 170.1, 170.3, 170.6, 170.7 (4×C(O)—CH$_3$).

MS (ESI): m/z (%)=869 (100) [M+Na]$^+$, 1715 (33) [2M+Na]$^+$.

| C$_{45}$H$_{42}$N$_4$O$_{13}$ (846.84). | calc.: | C: 63.81 | H: 5.00 | N: 6.62 |
| | found: | C: 63.53 | H: 5.27 | N: 6.46 |

{2-chloro-4-[5'-((1H-indole-2"-carbonyl)-amino)-1H-indole-2'-carbonyl]-1,2,3,4-tetrahydro-benzo[f]quinolin-6-yl}-2*,3*,4*,6*-tetra-O-acetyl-β-D-galactopyranoside (6)

Solid triphenylphosphane (557 mg, 2.13 mmoles, 6 equivs.) was added to a solution of the alcohol 5 (300 mg, 354 µmoles) in a mixture of absolute CCl$_4$ and CH$_3$CN (1:1, 12 ml) and the reaction mixture was stirred for four hours at 40° C. After addition of about three spatula amounts of silica gel the solvent was removed in vacuo and the residue was chromatographed with toluene/acetone=2:1. A total of 226 mg (74%) of a mixture of the desired chloride 6 and the corresponding elimination product (ratio ca. 2:1) was thereby obtained, from which, after renewed chromatography (PE/EE=1:1→3:1), 116 mg (38%) of the diastereomer-pure chloride 6a could be isolated as a pale yellow solid. The combined mixed fractions consisting of the second diastereomer and the corresponding elimination product were separated by semi-preparative HPLC (conditions see below). The product fractions thereby obtained were saturated with water, extracted three times with CH$_2$Cl$_2$ and the combined organic phases were finally concentrated by evaporation-in vacuo. Any traces of water present were removed by azeotropic distillation with benzene.

Analytical Data for the First Diastereomer 6a:

R$_f$=0.13 (PE/EE =1:1).

UV (CH$_3$CN): λ$_{max}$ (lg ε)=213 nm (3.804), 239 (3.695), 311 (3.673).

IR (KBr): ñ=3348 cm$^{-1}$ (NH), 3074 (Ar—H), 2934 (CH), 1752 (C=O), 1621 (C=C), 1598, 1370, 1230, 747.

$^1$H-NMR (300 MHz, acetone-d$_6$): δ=1.94, 1.96, 2.00, 2.15 (4×s, 12H, 4×C(O)CH$_3$), 3.47–3.56 (m, 2H, 1-H$_2$), 3.76–4.10 (m, 3H, 5*-H, 6*-H$_2$), 4.14 (dd, J=12.8, 7.2 Hz, 1H, 3-H$_a$), 4.59 (d, J=8.3 Hz, 1H, 1*-H), 4.67 (dd, J=12.8, 2.6 Hz, 1H, 3-H$_b$), 4.85 (dd, J=10.5, 3.4 Hz, 1H, 3*-H), 4.49–5.02 (m, 1H, 2-H), 5.35 (d, J=3.0 Hz, 1H, 4*-H), 5.41 (dd, J=10.5, 8.3 Hz, 1H, 2*-H), 6.80 (s, 1H, 3'-H), 6.97 (s, 1H, 5-H), 7.11 (ddd, J=7.9, 7.9, 1.1Hz, 1H, 5"-H), 7.26 (ddd, J=7.2, 7.2, 1.1 Hz, 1H, 6"-H), 7.37 (s, 1H, 3"-H), 7.53–7.71 (m, 6 H, 4"-H, 7"-H, 6'-H, 7'-H, 8-H, 9-H), 8.01–8.08 (m, 2H, 7-H, 10 H), 8.31 (d, J=1.9 Hz, 1H, 4'-H), 9.52 (s, 1H, 5'-NH), 10.92 (s, 1H, indole-NH), 10.96 (s, 1H, indole-NH).

$^{13}$C-NMR (75 MHz, acetone-d$_6$): δ=20.53 (3×CHOC(O)CH$_3$), 20.70 (CH$_2$OC(O)CH$_3$), 35.02 (C-1), 51.37 (C-3), 54.85 (C-2), 61.84 (C-6*), 67.83 (C-4*), 69.05 (C-2*), 71.36 (C-3*), 71.59 (C-5*), 101.5 (C-1*), 103.7 (C-3"), 108.4 (C-3'), 109.1 (C-5), 113.1, 113.2 (C-6', C-7'), 113.9 (C-4'), 116.3 (C-10b), 120.4, 120.9, 122.6, 122.7, 123.7, 124.7, 126.1, 128.4 (C-7, C-8, C-9, C-10, C-4", C-5", C-6", C-7"), 128.1 (C-6a), 128.7, 128.8 (C-3'a, C-3"a), 132.4, 132.9, 133.1, 133.4, 134.6, 136.4, 137.8 (C-10a, C-5', C-2', C-2", C-7'a, C-7"a, C-4a), 152.1 (C-6), 160.6 (2'-C =O), 164.0 (2"-C=O), 170.1, 170.3, 170.6, 170.7 (4×C(O)—CH$_3$).

MS (DCI, NH$_3$): m/z (%)=882 (100) [M+NH$_4$]$^+$, 865 (22) [M+H]$^+$.

| C$_{45}$H$_{41}$N$_4$O$_{12}$Cl (865.29). | calc.: | C: 62.46 | H: 4.78 |
| | found: | C: 62.14 | H: 5.14 |

| Analytical data for the second diastereomer 6b: | | |
|---|---|---|
| HPLC (semi-preparative): | column: | Kromasil 100 C18, 5 µm, 250 × 8 mm |
| | eluent: | 72% methanol in H$_2$O; 2.0 ml/min |
| | Rt: | 29.74 min |

$^1$H-NMR (300 MHz, acetone-d$_6$): δ=1.87, 1.94, 1.98, 2.10 (4×s, 12H, 4×C(O)CH$_3$), 3.50–3.56 (m, 2H, 1-H$_a$, 3-H$_a$), 3.87 (dd, J=18.1, 5.6 Hz, 1H, 1-H$_b$), 3.97–4.03 (m, 3H, 5*-H, 6*-H$_2$), 4.32 (d, J=7.9 Hz, 1H, 1*-H), 4.65 (dd, J=10.6, 3.4 Hz, 1H, 3*-H), 4.93 (dd, J=13.2, 3.8 Hz, 1H, 3-H$_b$), 5.10 (m$_c$, 1H, 2-H), 5.27 (dd, J=3.8, 1.2 Hz, 1H, 4*-H), 5.32 (dd, J=10.6, 7.9 Hz, 1H, 2*-H), 6.73 (d, J=1.9 Hz, 1H, 3'-H), 6.83 (s, 1H, 5-H), 7.05–7.10 (m, 1H, 5"-H), 7.19–7.25 (m, 1H, 6"-H), 7.30 (d, J=1.9 Hz, 1H, 3"-H), 7.50–7.67 (m, 6 H, 4"-H, 7"-H, 6'-H, 7'-H, 8-H, 9-H), 7.95–8.00 (m, 2H, 7-H, 10-H), 8.28 (s,1H, 4'-H), 9.37 (s, 1H, 5'-NH), 10.74 (s$_{br}$, 1H, indole-NH), 10.84 (s$_{br}$, 1H, indole-NH).

$^{13}$C-NMR (125 MHz, acetone-d$_6$): δ=20.47, 20.48, 20.58, 20.71 (4×C(O)CH$_3$), 34.66 (C-1), 50.81 (C-3), 55.94 (C-2), 62.10 (C-6*), 67.87 (C-4*), 68.86 (C-2*), 71.38 (C-3*), 71.61 (C-5*), 101.6 (C-1*), 103.6 (C-3"), 108.5 (C-3'), 108.9 (C-5), 113.1, 113.3 (C-6', C-7'), 113.9 (C-4'), 114.9 (C-10b), 120.4, 120.9, 122.5, 122.6, 123.7, 124.7, 126.1, 128.4 (C-7, C-8, C-9, C-10, C-4", C-5", C-6", C-7"), 124.5 (C-6a), 128.1, 128.8 (C-3'a, C-3"a), 132.5, 133.0, 133.2, 133.6, 134.6, 136.4, 137.9 (C-10a, C-5', C-2', C-2", C-7'a, C-7"a, C-4a), 152.2 (C-6), 160.5 (2'-C=O), 164.4 (2"-C=O), 170.2, 170.3, 170.6 170.7 (4×C(O)—CH$_3$).

rac-{2-chloro-4-[5'-((1H-indole-2"-carbonyl)-amino)-1H-indole-2'-carbonyl]-1,2,3,4-tetrahydrobenzo[f]quinolin-6-yl}-β-D-galactopyranoside (7):

The acetyl-protected galactoside 6 (40.0 mg, 46.2 µmoles) was dissolved in absolute methanol (1.5 ml) and NaOMe (3.77 µl of a 5.4 M solution in MeOH, 20.3 µmoles, 0.44 equiv.) was added at 0° C. After discontinuing the cooling the reaction mixture was stirred for 30 minutes at room temperature and the product was then precipitated by adding water. The precipitate was filtered off with a P2 frit and washed with water. In order to remove traces of water the solid was suspended three times in toluene and the solvent was removed in vacuo. 30.5 mg (95%) of deprotected galactoside 7 were obtained in the form of a pale yellowish solid.

$R_f$=0.28 (EE/MeOH=10:1)

UV (CH$_3$CN) : $\lambda_{max}$ (lg ϵ)=215 nm (3.575), 310 (3.431).

IR (KBr): ñ=3406 cm$^{-1}$ (very broad, NH/OH), 3077 (Ar—H), 2924 (CH), 1622 (C=C), 1530, 14.04, 1233, 1074 748.

$^1$H-NMR (500 MHz, DMF-d$_7$): δ=3.28–3.31 (m, 2H, 3*-H, 5*-H), 3.47 (dd, J=17.6, 4.8 Hz, 1H, 1-H$_a$), 3.58 (dd, J=11.0, 6.0 Hz, 1H, 6*-H$_a$), 3.65 (dd, J=11.0, 6.4 Hz, 1H, 6*-H$_b$), 3.82–3.88 (m, 2H, 2*-H, 4*-H, 1-H$_b$), 4.43 (dd, J=12.8, 6.4 Hz, 1H, 3-H$_a$), 4.45–4.49 (m, 2H, 1*-H, 3-H$_b$), 5.01–5.05 (m, 1H, 2-H), 6.82 (d, J=1.4 Hz, 1H, 3'-H), 7.09 (ddd, J=6.9, 6.9, 0.9 Hz, 1H, 5"-H), 7.17 (s, 1H, 5-H), 7.25 (ddd, J=7.1, 6.9, 1.0 Hz, 1H, 6"-H), 7.48 (m, 3H, 3"-H, 7'-H, 8-H), 7.58–7.64 (m, 2H, 7"-H, 9-H), 7.68 (d, J=6.9 Hz, 1H, 4"-H), 7.69 (d, J=6.9, 1.9 Hz, 1H, 6'-H), 7.97 (d, J=8.5 Hz, 1H, 10-H), 8.19 (d, J=1.9 Hz, 1H, 4'-H), 8.37 (d, J=8.5 Hz, 1H, 7-H), 10.20 (s, 1H, 5'-NH), 11.67 (s, 2H, 2×indole-NH).

$^{13}$C-NMR (125 MHz, DMF-d$_7$): δ=39.33 (C-1), 51.87 (C-3), 55.54 (C-2), 61.53 (C-6*), 69.30, 71.69 (C-4*, C-2*), 74.54 (C-3*), 76.22 (C-5*), 103.9 (C-1*, C-3"), 107.4 (C-3'), 108.9 (C-5), 112.9, 113.0 (C-7', C-7"), 113.4 (C-4'), 114.4 (C-10b), 119.6 (C-6'), 120.5 (C-5"), 122.3 (C-4"), 123.2 (C-7), 123.5 (C-10), 124.2 (C-6"), 124.8 (C-6a), 125.2 (C-8), 127.8 (C-9), 128.5, 128.8 (C-3'a, C-3"a), 129.6 (C-7'a), 132.6, 133.0, 133.1, 134.7, (C-10a, C-5', C-2', C-2"), 136.5, 137.8 (C-7"a, C-4a), 152.4 (C-6), 160.5 (2'-C=O), 164.5 (2"-C=O).

MS (FAB): m/z (%)=695 (100) [M−H]$^-$.

| C$_{37}$H$_{33}$N$_4$O$_8$Cl (697.14). | calc.: | C: 63.75 | H: 4.77 |
| | found: | C: 63.71 | H: 4.85 |
| Analytical HPLC for determination of the purity: | column: | Kromasil 100 C18 | |
| | eluent: | 62% MeOH in H$_2$O; 0.7 ml/min | |
| | RT: | 41.65 min | |

The invention claimed is:

1. 5-hydroxy-1,2-dihydro-3H-pyrrolo[3,2-e]indoles of the general formula (II) or 5-hydroxy-1,2-dihydro-3H-benzo[e]indoles of the general formula (III), or their O-glycosides with monosaccharides, disaccharides or oligosaccharides of the general formulae (V) and (VI):

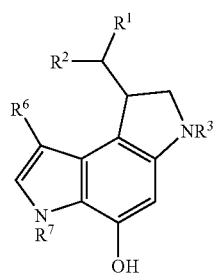

II

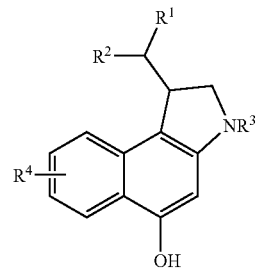

III

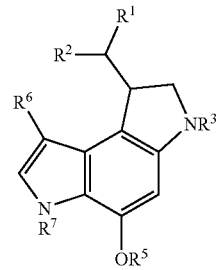

V

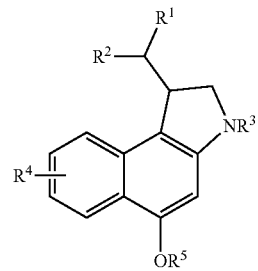

VI wherein in the general formulae (II), (III), (V) and (VI)

$R^1$ denotes halogen $R^2$ denotes straight-chain or branched alkyl with up to 8 carbon atoms, which is optionally substituted by phenyl, hydroxy, straight-chain or branched alkoxy with up to 6 carbon atoms, $R^3$ denotes straight-chain or branched alkyl with up to 8 carbon atoms, which is optionally substituted by phenyl, hydroxy, straight-chain or branched alkoxy with up to 6 carbon atoms, or denotes a group of the formula —SO$_2$R$^8$, —CO—R$^9$ or —CO$_2$R$^{10}$, wherein $R^8$ denotes straight-chain or branched alkyl with up to 6 carbon atoms, benzyl or phenyl, the latter optionally being substituted by straight-chain or branched alkyl with up to 6 carbon atoms, and $R^9$ denotes straight-chain or branched alkyl with up to 8 carbon atoms, which is optionally substituted by carboxy, straight-chain or branched alkoxycarbonyl with up to 6 carbon atoms, or by a group of the formula —CO—NR$^{11}$R$^{12}$, wherein the radicals R$^{11}$ and R$^{12}$ together form a biradical of one of the following formulae

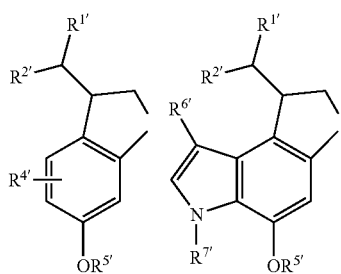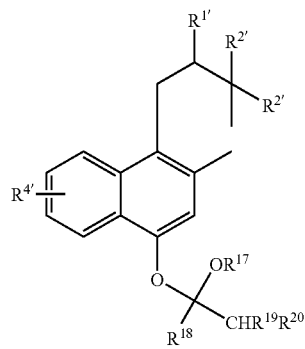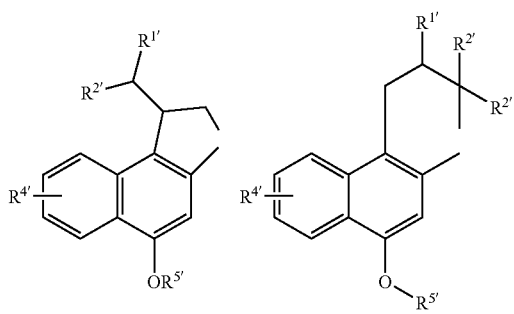
wherein R$^{1'}$, R$^{2'}$, R$^{4'}$, R$^{5'}$, R$^{6'}$ and R$^{7'}$ have the meanings of R$^1$, R$^2$, R$^4$, R$^5$, R$^6$ and R$^7$
given above and hereinafter, wherein R$^{2'}$ also denotes hydrogen,
R$^{10}$ denotes hydrogen or straight-chain or branched alkyl with up to 6 carbon atoms,
or
R$^3$ denotes a radical of one of the formulae
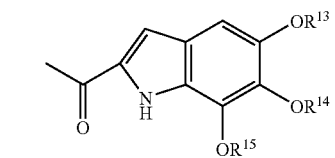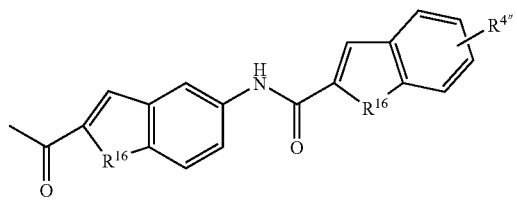
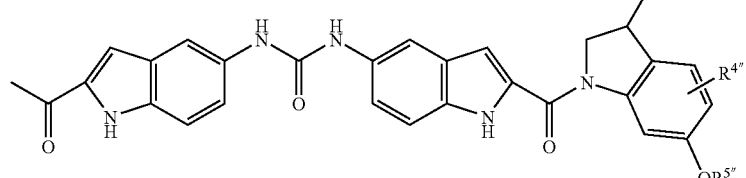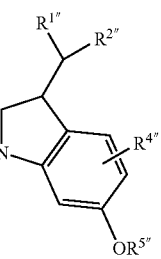
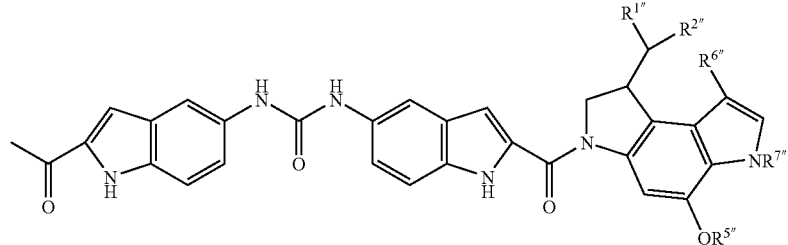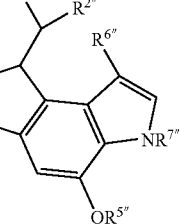
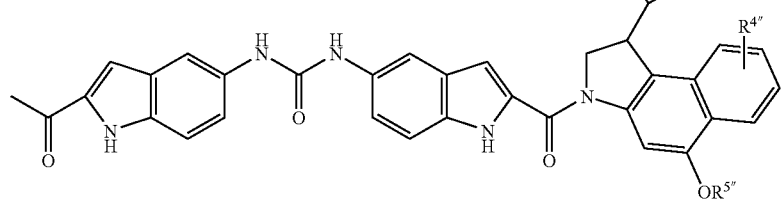

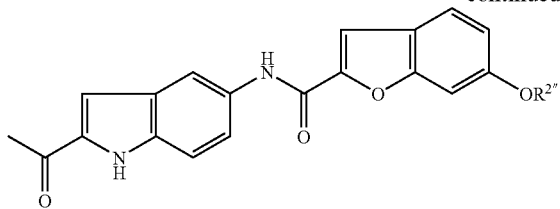

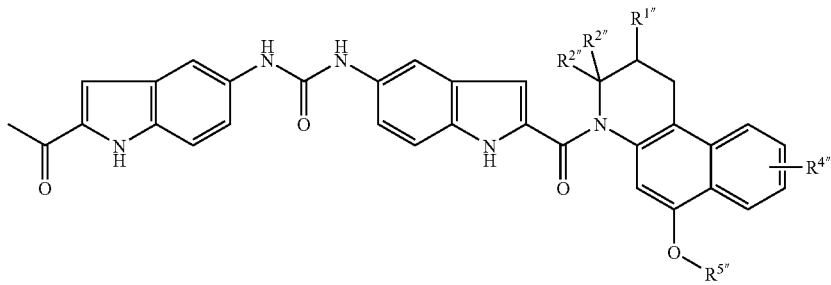

wherein

R[1″], R[2″] have the meanings of R[1], R[2] given above,

R[4″] denotes hydrogen or straight-chain or branched alkyl with up to 8 carbon atoms, which is also optionally substituted by hydroxy, carboxy, phenyl or by straight-chain or branched alkoxy, acyl or alkoxycarbonyl with in each case up to 6 carbon atoms, or denotes a hydroxy or amino group that is optionally substituted by straight-chain or branched alkyl, acyl or alkoxycarbonyl with in each case up to 6 carbon atoms, R[5″] denotes a monosaccharide, disaccharide or oligosaccharide of hexoses or pentoses or heptoses, that may also be included among the group of desoxy sugars or amino sugars and belong to the D-series or L-series and in the disaccharides or oligosaccharides are either identical or different, R[6″] and R[7″] are identical or different and denote hydrogen or straight-chain alkyl with up to 8 carbon atoms, R[4], R[5], R[6] and R[7] have the meanings of R[4″], R[5″], R[6″] and R[7″] given above, R[13], R[14] and R[15] are identical or different and denote hydrogen or straight-chain or branched alkyl or acyl with in each case up to 6 carbon atoms, R[16] denotes unsubstituted nitrogen, oxygen or sulfur, R[17] denotes a hydroxy-protective group, or straight-chain or branched alkyl with up to 8 carbon atoms that is optionally substituted by hydroxy, carboxyl, phenyl or by straight-chain or branched alkoxyl, acyl or alkoxycarbonyl with in each case up to 6 carbon atoms, and optionally together with R[4], R[5] or R[6] forms a ring, or denotes a sugar residue of the formula

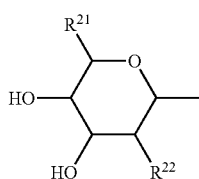 or

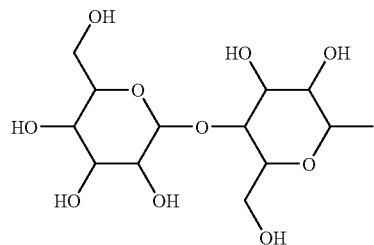

in the D or L form, wherein

R[21] denotes methyl or the —CH$_2$OH group and

R[22] denotes hydroxyl or a radical of the formula —NR[23]R[24], wherein

R[23] and R[24] are identical or different and denote hydrogen, straight-chain or branched alkyl with up to 6 carbon atoms or an amino-protective group, and wherein the hydroxyl groups of the sugar residues are optionally protected, R[18], R[19] and R[20] are identical or different and denote hydrogen or straight-chain or branched or cyclic alkyl with up to 8 carbon atoms that is optionally substituted by phenyl, halogen, azido, straight-chain or branched alkoxyl, alkoxycarbonyl or oxyacyl with in each case up to 6 carbon atoms, hydroxyl, carbonyl or by a group of the formula —NR[23]R[24], wherein R[23] and R[24] have the meaning given above.

2. A compound of the general formula (II), (III), (V) or (VI) according to claim 1, wherein R[1] denotes chlorine, bromine or iodine, R[2] denotes straight-chain or branched alkyl with up to 8 carbon atoms that is optionally substituted by phenyl, hydroxy, straight-chain or branched alkoxy with up to 4 carbon atoms, $R^3$ denotes straight-chain or branched alkyl with up to 6 carbon atoms, which is optionally substituted by phenyl, hydroxy, straight-chain or branched alkoxy with up to 4 carbon atoms, or denotes a group of the formula —$SO_2R^8$, —$COR^9$ or —$CO_2R^{10}$,
wherein
$R^8$ denotes straight-chain or branched alkyl with up to 4 carbon atoms, benzyl or phenyl, wherein the latter are optionally substituted by straight-chain or branched alkyl with up to 4 carbon atoms, and
$R^9$ denotes straight-chain or branched alkyl with up to 6 carbon atoms which is optionally substituted by carboxy, straight-chain or branched alkoxycarbonyl with up to 4 carbon atoms, or by a group of the formula —CO—$NR^{11}R^{12}$,
wherein
$R^{11}$ and $R^{12}$ together form a biradical of one of the following formulae

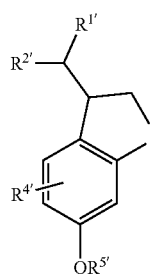 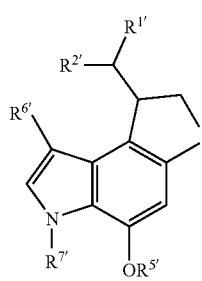

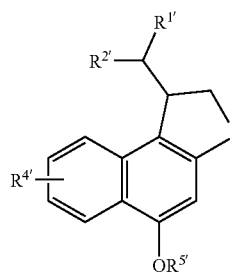

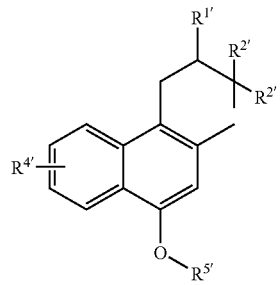

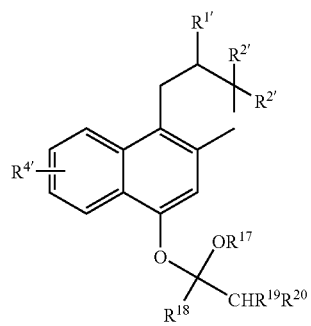

wherein
$R^{1'}$, $R^{2'}$ have the meanings of $R^1$, $R^2$ given above, wherein $R^{2'}$ also denotes a hydrogen atom,
$R^{4'}$ denotes hydrogen or straight-chain or branched alkyl with up to 6 carbon atoms or denotes a hydroxy or amino group that is optionally substituted by a straight-chain or branched alkyl, acyl or alkoxycarbonyl with in each case up to 6 carbon atoms,
$R^{5'}$ denotes a monosaccharide or a disaccharide of hexoses or pentoses that may also be included among the group of desoxy sugars or amino sugars and belong to the D-series or L-series and may be either identical or different in the disaccharide,
$R^{6'}$ and $R^{7'}$ are identical or different and denote hydrogen or straight-chain alkyl with up to 8 carbon atoms,
$R^{10}$ denotes hydrogen or straight-chain or branched alkyl with up to 6 carbon atoms,
or
$R^3$ denotes a radical of one of the formulae

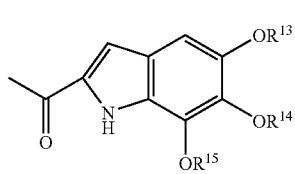 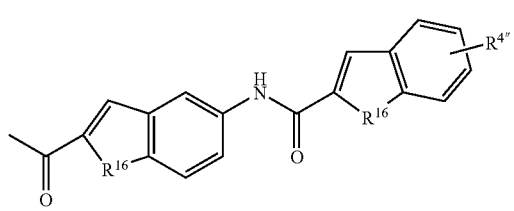

-continued

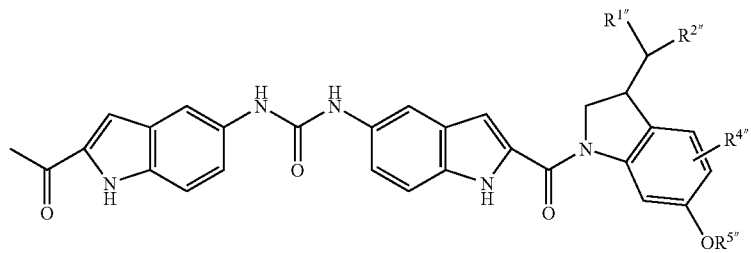

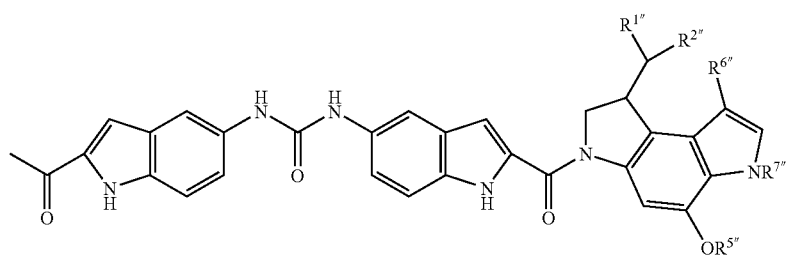

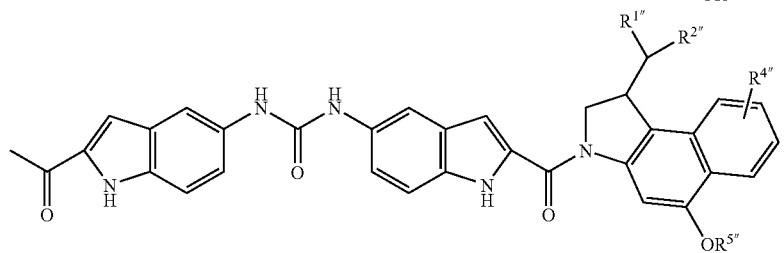

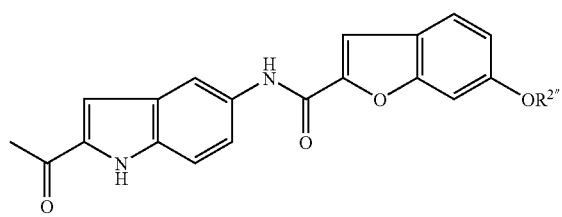

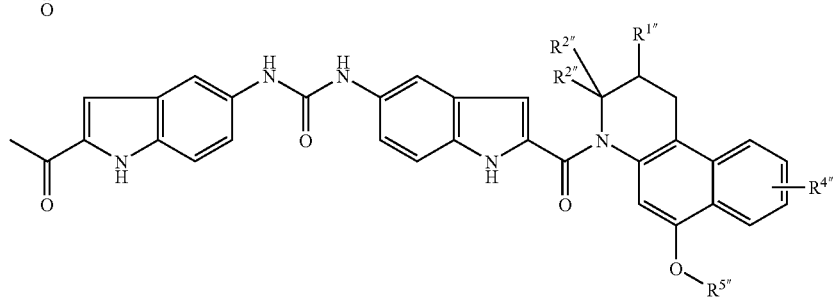

wherein
R$^{1''}$, R$^{2''}$ have the meanings of R$^1$, R$^2$ given above,
R$^{4''}$, R$^{5''}$, R$^{6''}$ and R$^{7''}$ have the meanings of R$^{4'}$, R$^{5'}$, R$^{6'}$ and R$^{7'}$ given above,
R$^{13}$, R$^{14}$ and R$^{15}$ are identical or different and denote hydrogen or straight-chain or branched alkyl or acyl with in each case up to 6 carbon atoms,
R$^{16}$ denotes unsubstituted nitrogen, oxygen or sulfur,
R$^4$ denotes hydrogen or straight-chain or branched alkyl with up to 6 carbon atoms or denotes a hydroxy or amino group that is optionally substituted by a straight-chain or branched alkyl, acyl or alkoxycarbonyl with in each case up to 6 carbon atoms, R$^5$ denotes a monosaccharide or a disaccharide of hexoses or pentoses that may also be included among the group of desoxy sugars or amino sugars and belong to the D-series or L-series and may be either identical or different in the disaccharide,
R$^6$ and R$^7$ are identical or different and denote hydrogen or straight-chain alkyl with up to 8 carbon atoms,
R$^{17}$ denotes a hydroxy-protective group, or straight-chain or branched alkyl with up to 8 carbon atoms that is optionally substituted by hydroxy, carboxyl, phenyl or by straight-chain or branched alkoxyl, acyl or alkoxycarbonyl with in each case up to 6 carbon atoms, and optionally together with R⁴, R⁵ or R⁶ forms a ring, or denotes a sugar residue of the formula

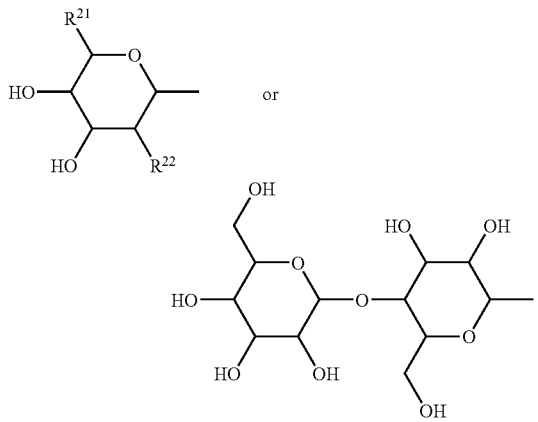

in the D or L form,
wherein
R²¹ denotes methyl or the —CH₂OH group and
R²² denotes hydroxyl or a radical of the formula —NR²³R²⁴, wherein
R²³ and R²⁴ are identical or different and denote hydrogen, straight-chain or branched alkyl with up to 6 carbon atoms or an amino-protective group, and wherein the hydroxy groups of the sugar residues are optionally protected, R¹⁸, R¹⁹ and R²⁰ are identical or different and denote hydrogen or straight-chain or branched or cyclic alkyl with up to 8 carbon atoms, which is optionally substituted by phenyl, halogen, azido, straight-chain or branched alkoxyl, alkoxycarbonyl or oxyacyl with in each case up to 6 carbon atoms, hydroxyl, carboxyl or by a group of the formula —NR²³R²⁴, wherein R²³ and R²⁴ have the meaning given above.

3. A compound of the general formula (II), (III), (V) or (VI) according to claim 1, wherein R¹ denotes chlorine, R² denotes straight-chain or branched alkyl with up to 4 carbon atoms that is optionally substituted by phenyl, hydroxy, straight-chain or branched alkoxy with up to 3 carbon atoms, R³ denotes straight-chain or branched alkyl with up to 4 carbon atoms that is optionally substituted by phenyl, hydroxy, straight-chain or branched alkoxy with up to 3 carbon atoms, or denotes a group of the formula —SO₂R⁸, wherein R⁸ denotes methyl, benzyl or phenyl, the latter optionally being substituted by methyl or ethyl or R³ denotes a radical or one of the formulae

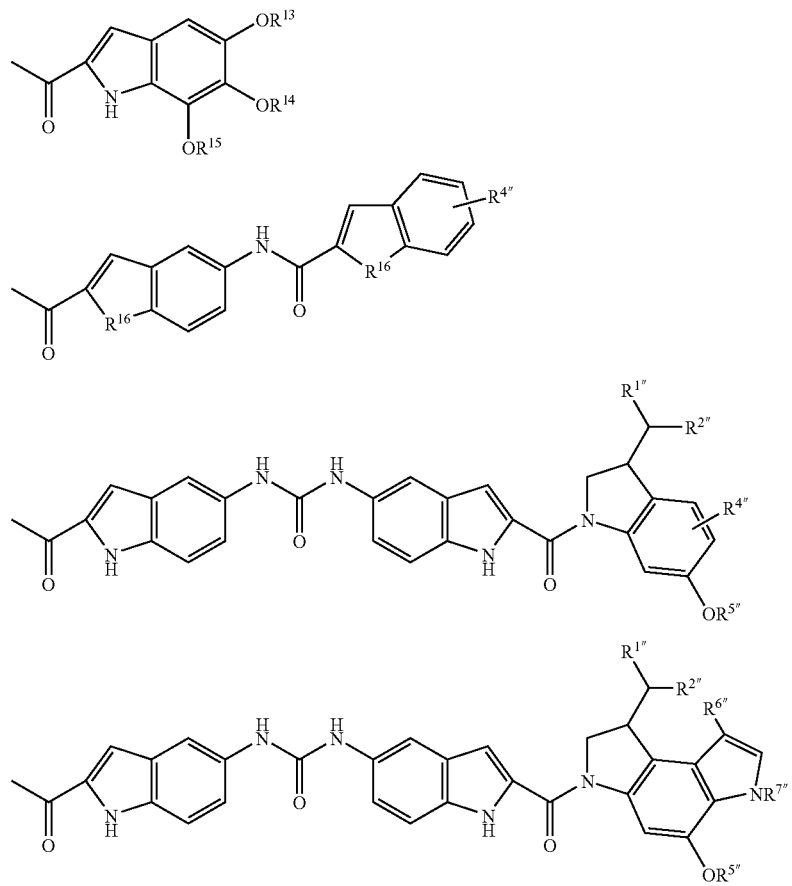

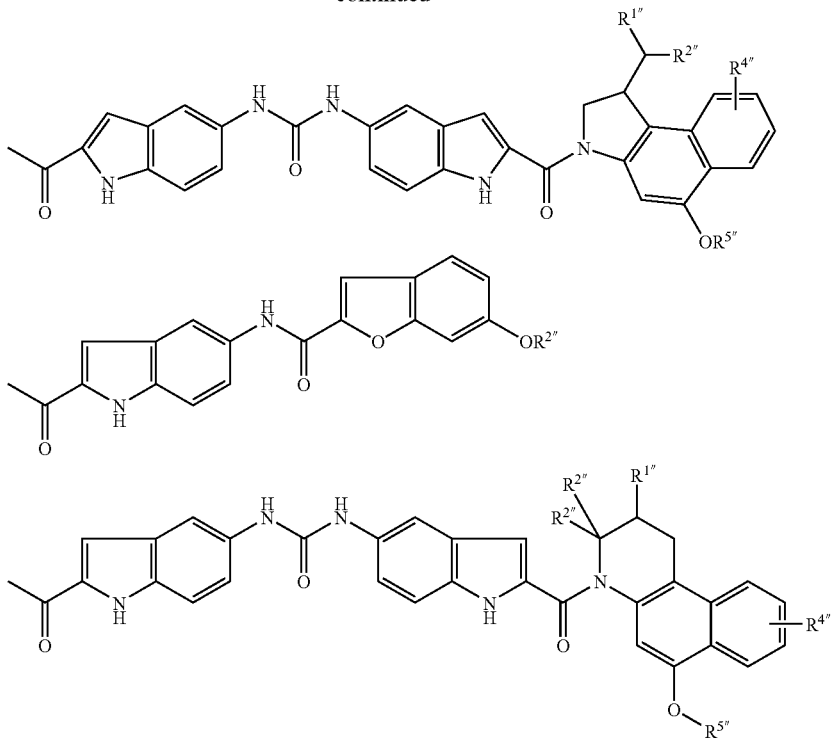

wherein
- $R^{1''}$, $R^{2''}$, $R^{4''}$, $R^{5''}$, $R^{6''}$ and $R^{7''}$ have the meanings of $R^1$, $R^2$, $R^4$, $R^5$, $R^6$ and $R^7$ given above and hereinafter,
- $R^{13}$, $R^{14}$ and $R^{15}$ are identical or different and denote hydrogen, methyl, ethyl or acetyl,
- $R^{16}$ denotes unsubstituted nitrogen, oxygen or sulfur,
- $R^4$ denotes hydrogen,
- $R^5$ denotes α-D-mannose, β-D-galactose, β-D-glucuronic acid and β-D-glucose,
- $R^6$ and $R^7$ are identical or different and denote hydrogen or a straight-chain or branched alkyl with up to 4 carbon atoms.

4. A treatment agent containing a pharmaceutically acceptable carrier and one or more compounds selected from 5-hydroxy-1,2-dihydro-3H-pyrrolo[3,2-e]indoles of the general formula (II) or 5hydroxy-1,2dihydro-3H-benzo[e] indoles of the general formula (III), or their O-glycosides with monosaccharides, disaccharides or oligosaccharides of the general formulae (V) and (VI):

II

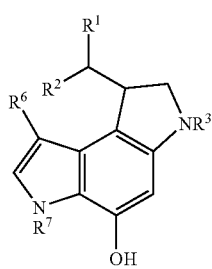

-continued

III

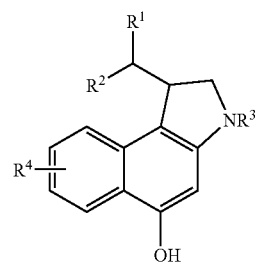

V

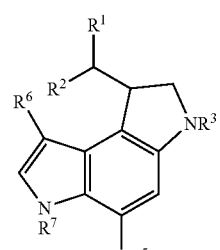

VI

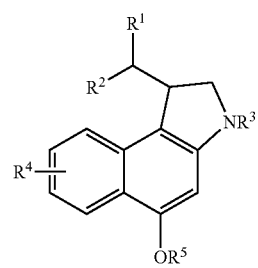

wherein in the general formulae (II), (III), (V) and (VI)
$R^1$ denotes halogen,
$R^2$ denotes straight-chain or branched alkyl with up to 8 carbon atoms, which is optionally substituted by phenyl, hydroxy, straight-chain or branched alkoxy with up to 6 carbon atoms,
$R^3$ denotes straight-chain or branched alkyl with up to 8 carbon atoms, which is optionally substituted by phenyl, hydroxy, straight-chain or branched alkoxy with up to 6 carbon atoms, or denotes a group of the formula $-SO_2R^8$, $-CO-R^9$ or $-CO_2R^{10}$,
wherein
$R^8$ denotes straight-chain or branched alkyl with up to 6 carbon atoms, benzyl or phenyl, the latter optionally being substituted by straight-chain or branched alkyl with up to 6 carbon atoms,
and
$R^9$ denotes straight-chain or branched alkyl with up to 8 carbon atoms, which is optionally substituted by carboxy, straight-chain or branched alkoxycarbonyl with up to 6 carbon atoms, or by a group of the formula $-CO-NR^{11}R^{12}$, wherein the radicals $R^{11}$ and $R^{12}$ together form a biradical of one of the following formulae

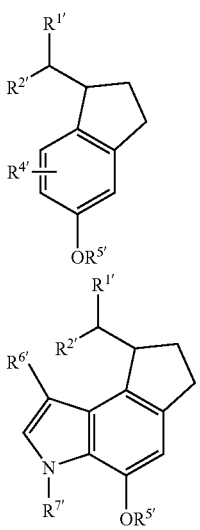

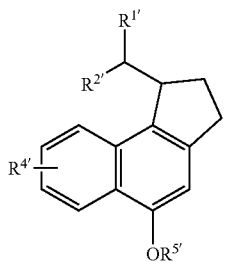

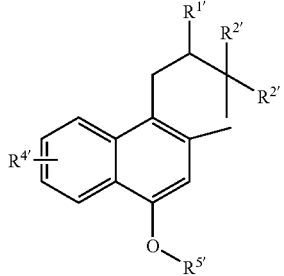

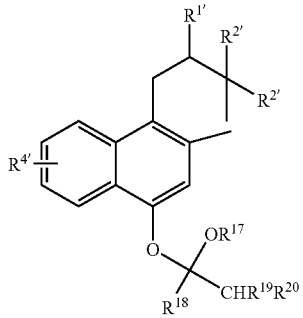

wherein $R^{1'}$, $R^{2'}$, $R^{4'}$, $R^{5'}$, $R^{6'}$ and $R^{7'}$ have the meanings of $R^1$, $R^2$, $R^4$, $R^5$, $R^6$ and $R^7$ given above and hereinafter, wherein $R^2$ also denotes hydrogen, $R^{10}$ denotes hydrogen or straight-chain or branched alkyl with up to 6 carbon atoms, or $R^3$ denotes a radical or one of the formulae

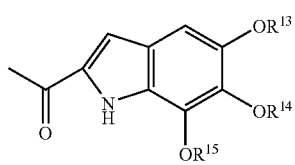

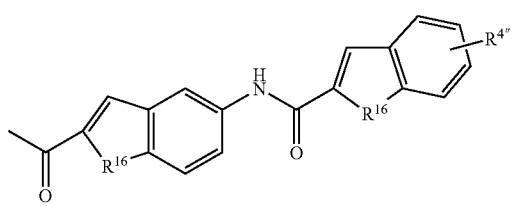

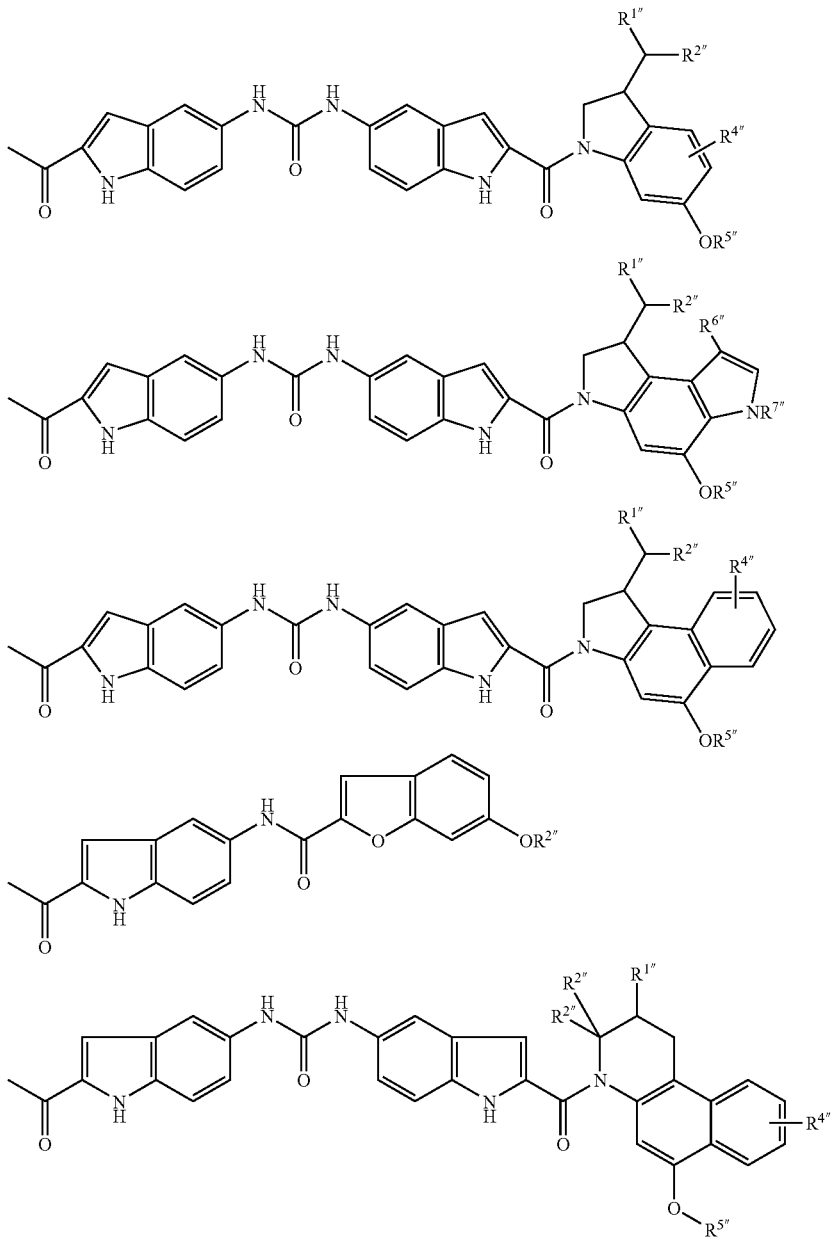

wherein
R[1"'], R[2"'] have the meanings of R[1], R[2] given above,
R[4"] denotes hydrogen or straight-chain or branched alkyl with up to 8 carbon atoms, which is also optionally substituted by hydroxy, carboxy, phenyl or by straight-chain or branched alkoxy, acyl or alkoxycarbonyl with in each case up to 6 carbon atoms, or denotes a hydroxy or amino group that is optionally substituted by straight-chain or branched alkyl, acyl or alkoxycarbonyl with in each case up to 6 carbon atoms,
R[5"] denotes a monosaccharide, disaccharide or oligosaccharide of hexoses or pentoses or heptoses, that may also be included among the group of desoxy sugars or amino sugars and belong to the D-series or L-series and in the disaccharides or oligosaccharides are either identical or different,
R[6"] and R[7"] are identical or different and denote hydrogen or straight-chain alkyl with up to 8 carbon atoms,
R[4], R[5], R[6] and R[7] have the meanings of R[4"], R[5"], R[6"] and R[7"] given above,
R[13], R[14] and R[15] are identical or different and denote hydrogen or straight-chain or branched alkyl or acyl with in each case up to 6 carbon atoms,
R[16] denotes unsubstituted nitrogen, oxygen or sulfur,
R[17] denotes a hydroxy-protective group, or straight-chain or branched alkyl with up to 8 carbon atoms that is optionally substituted by hydroxy, carboxyl, phenyl or by straight-chain or branched alkoxyl, acyl or alkoxycarbonyl with in each case up to 6 carbon atoms, and optionally together with $R^4$, $R^5$ or $R^6$ forms a ring, or denotes a sugar residue of the formula

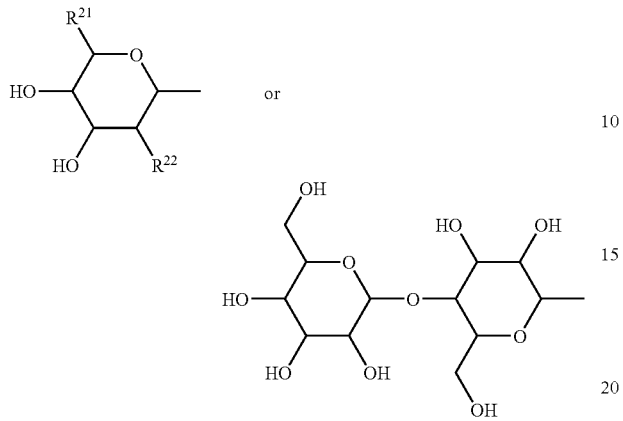

in the D or L form,
wherein
$R^{21}$ denotes methyl or the —CH$_2$OH group and
$R^{22}$ denotes hydroxyl or a radical of the formula —NR$^{23}$R$^{24}$, wherein
$R^{23}$ and $R^{24}$ are identical or different and denote hydrogen, straight-chain or branched alkyl with up to 6 carbon atoms or an amino-protective group, and wherein the hydroxyl groups of the sugar residues are optionally protected,
$R^{18}$, $R^{19}$ and $R^{20}$ are identical or different and denote hydrogen or straight-chain or branched or cyclic alkyl with up to 8 carbon atoms that is optionally substituted by phenyl, halogen, azido, straight-chain or branched alkoxyl, alkoxycarbonyl or oxyacyl with in each case up to 6 carbon atoms, hydroxyl, carbonyl or by a group of the formula —NR$^{23}$R$^{24}$, wherein $R^{23}$ and $R^{24}$ have the meaning given above.

5. A process for the production of a treatment agent, comprising:

deprotonating an organic compound of the general formula (X) or (XI) at the nitrogen atom of the —NHR$^3$ group with a suitable base;

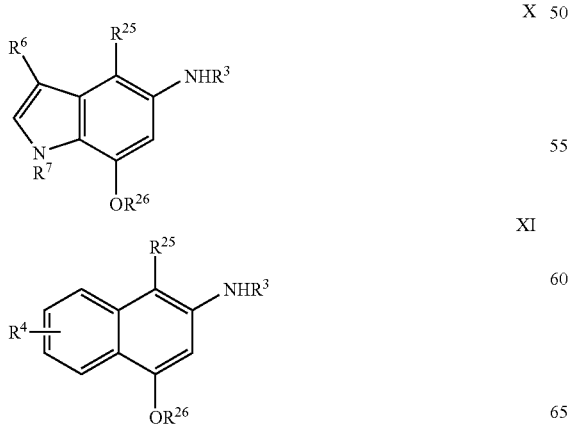

wherein
$R^{25}$ denotes bromine or iodine,
$R^{26}$ denotes one of the hydroxy-protective groups specified above,
$R^3$ denotes straight-chain or branched alkyl with up to 8 carbon atoms, which is optionally substituted by phenyl, hydroxy, straight-chain or branched alkoxy with up to 6 carbon atoms, or denotes a group of the formula —SO$_2$R$^8$, —CO—R$^9$ or —CO$_2$R$^{10}$,
wherein
$R^8$ denotes straight-chain or branched alkyl with up to 6 carbon atoms, benzyl or phenyl, the latter optionally being substituted by straight-chain or branched alkyl with up to 6 carbon atoms,
and
$R^9$ denotes straight-chain or branched alkyl with up to 8 carbon atoms, which is optionally substituted by carboxy, straight-chain or branched alkoxycarbonyl with up to 6 carbon atoms, or by a group of the formula —CO—NR$^{11}$R$^{12}$, wherein the radicals $R^{11}$ and $R^{12}$ together form a biradical of one of the following formulae

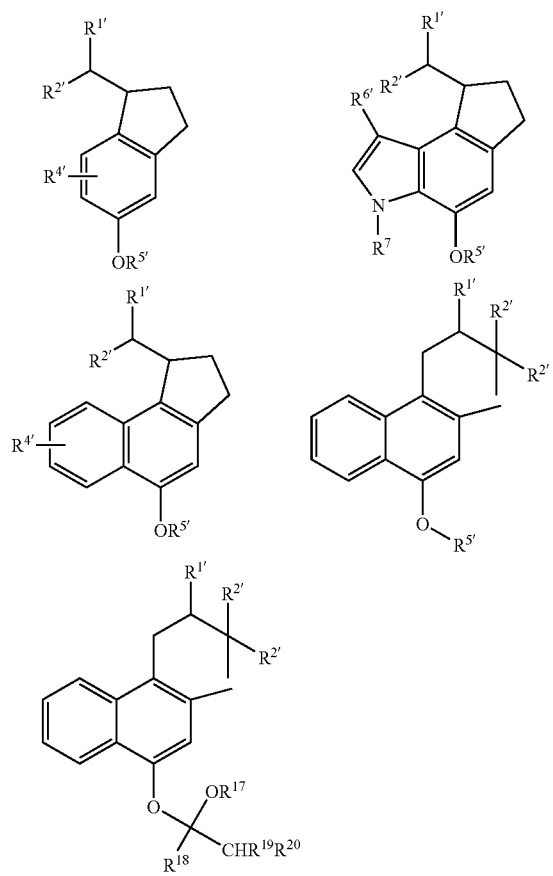

wherein $R^{1'}$, $R^{2'}$, $R^{4'}$, $R^{5'}$, $R^{6'}$ and $R^{7'}$ have the meanings of $R^1$, $R^2$, $R^4$, $R^5$, $R^6$ and $R^7$ given above and hereinafter, wherein $R^{2'}$ also denotes hydrogen,
$R^{10}$ denotes hydrogen or straight-chain or branched alkyl with up to 6 carbon atoms,
or
$R^3$ denotes a radical of one of the formulae

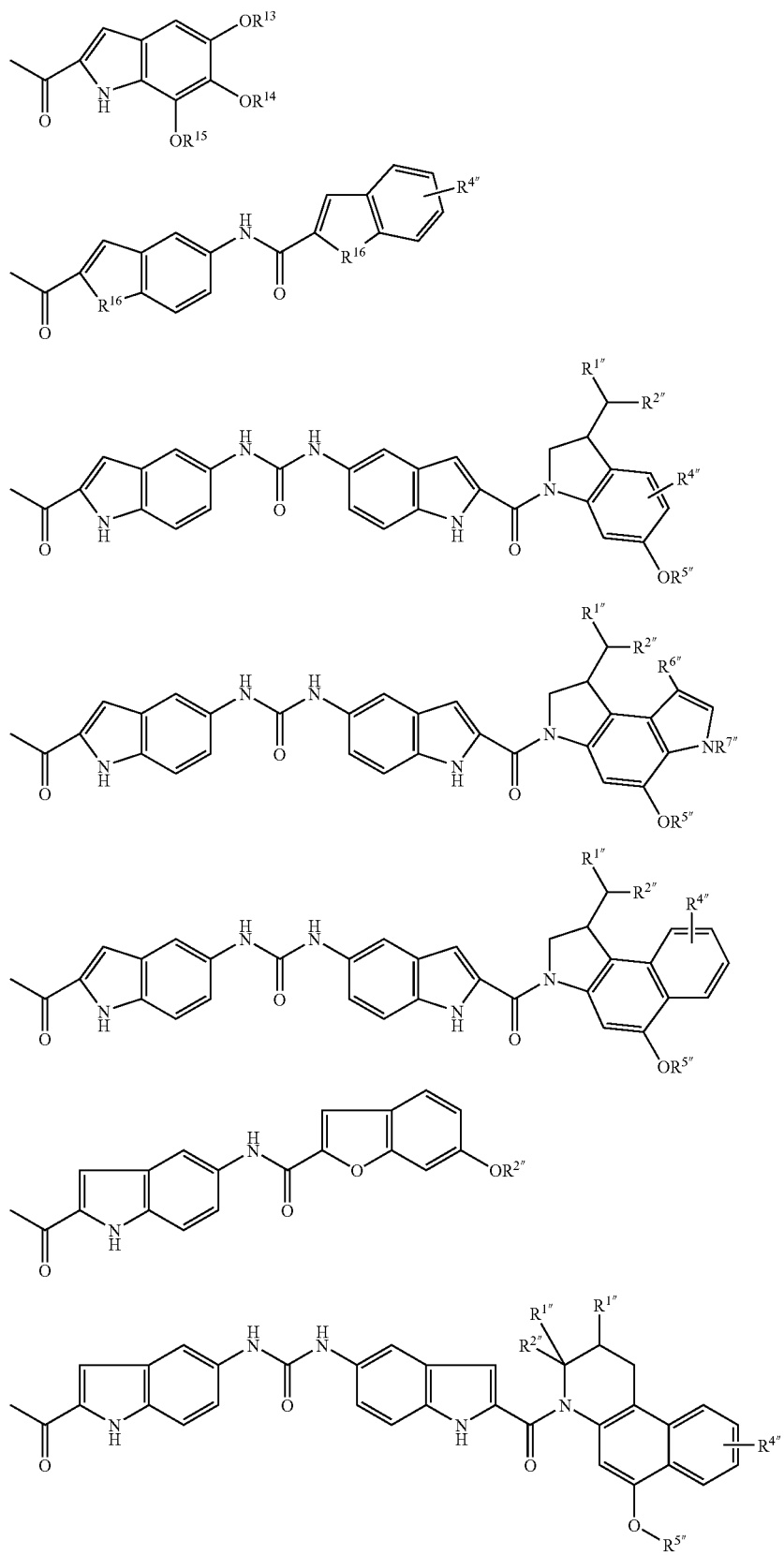

wherein

R$^1$ denotes halogen,

R$^2$ denotes straight-chain or branched alkyl with up to 8 carbon atoms, which is optionally substituted by phenyl, hydroxy, straight-chain or branched alkoxy with up to 6 carbon atoms, R$^{1''}$, R$^{2''}$ have the meanings of R$^1$, R$^2$ given above, R$^{4''}$ denotes hydrogen or straight-chain or branched alkyl with up to 8 carbon atoms, which is also optionally substituted by hydroxy, carboxy, phenyl or by straight-chain or branched alkoxy, acyl or alkoxycarbonyl with in each case up to 6 carbon atoms, or denotes a hydroxy or amino group that is optionally substituted by straight-chain or branched alkyl, acyl or alkoxycarbonyl with in each case up to 6 carbon atoms, R$^{5''}$ denotes a monosaccharide, disaccharide or oligosaccharide of hexoses or pentoses or heptoses, that may also be included among the group of desoxy sugars or amino sugars and belong to the D-series or L-series and in the disaccharides or oligosaccharides are either identical or different, R$^{6''}$ and R$^{7''}$ are identical or different and denote hydrogen or straight-chain alkyl with up to 8 carbon atoms, R$^4$, R$^5$, R$^6$ and R$^7$ have the meanings of R$^{4''}$, R$^{5''}$, R$^{6''}$ and R$^{7''}$ given above, R$^{13}$, R$^{14}$ and R$^{15}$ are identical or different and denote hydrogen or straight-chain or branched alkyl or acyl with in each case up to 6 carbon atoms, R$^{16}$ denotes unsubstituted nitrogen, oxygen or sulfur, R$^{17}$ denotes a hydroxy-protective group, or straight-chain or branched alkyl with up to 8 carbon atoms that is optionally substituted by hydroxy, carboxyl, phenyl or by straight-chain or branched alkoxyl, acyl or alkoxycarbonyl with in each case up to 6 carbon atoms, and optionally together with R$^4$, R$^5$ or R$^6$ forms a ring, or denotes a sugar residue of the formula

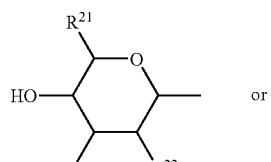

or

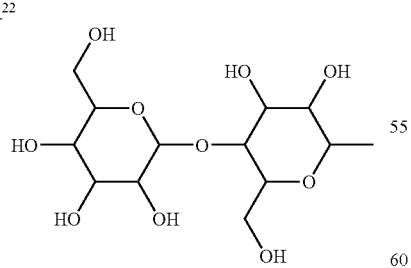

in the D or L form, wherein

R$^{21}$ denotes methyl or the —CH$_2$OH group and

R$^{22}$ denotes hydroxyl or a radical of the formula —NR$^{23}$R$^{24}$, wherein R$^{23}$ and R$^{24}$ are identical or different and denote hydrogen, straight-chain or branched alkyl with up to 6 carbon atoms or an amino-protective group, and wherein the hydroxyl groups of the sugar residues are optionally protected, R$^{18}$, R$^{19}$ and R$^{20}$ are identical or different and denote hydrogen or straight-chain or branched or cyclic alkyl with up to 8 carbon atoms that is optionally substituted by phenyl, halogen, azido, straight-chain or branched alkoxyl, alkoxycarbonyl or oxyacyl with in each case up to 6 carbon atoms, hydroxyl, carbonyl or by a group of the formula —NR$^{23}$R$^{24}$, wherein R$^{23}$ and R$^{24}$ have the meaning given above, reacting the deprotonated organic compound of the general formula (X) or (XI) with a compound of the general formula (XII) or (XIII), in the presence of an organic solvent to form a compound of the general formula (XV), (XVI), (XVIII) or (XIX),

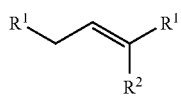
XII

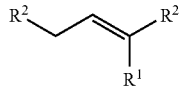
XIII wherein

R$^1$ has the meaning given above,

R$^2$ has the meaning given above,

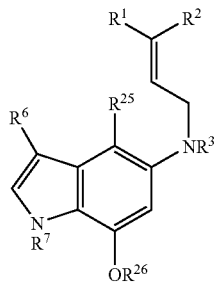
XV

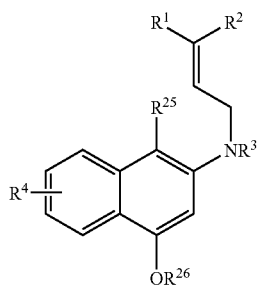
XVI

-continued

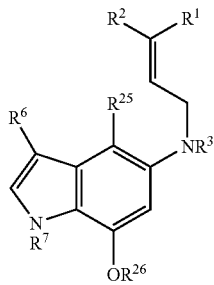
XVIII

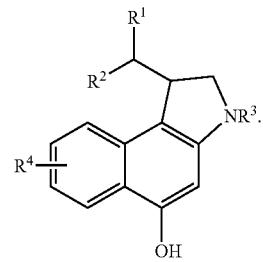
III

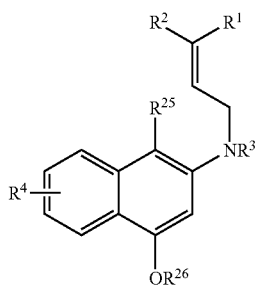
XIX wherein
R¹ has the meaning given above,
R² has the meaning given above,
R³ has the meaning given above,
R⁴, R⁶, R7, R²⁵ and R²⁶ have the meaning given above;
closing the compound of the general formula (XV), (XVI), (XVIII) or (XIX) to form a dihydropyrrole ring by a radical cyclisation using tributyltin hydride and a radical initiator; and
removing the protective group on the phenolic oxygen by hydrogenolysis in the presence of Pd/C and ammonium formate,
whereby a 5-hydroxy-1,2dihydro-3H-pyrrolo[3,2-e]indole of the general formula (II) or 5-hydroxy-1,2-dihydro-3H-benzo[e]indole of the general formula (III) is formed,

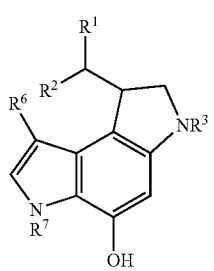
II

6. A process according to claim 5, wherein $R^1$ in the general formula (II) or (III) denotes chlorine.

7. A process according to claim 5, wherein $R^3$ in the general formula (II) or (III) denotes tert-butoxycarbonyl.

8. A process according to claim 5, further comprising:
reacting the compound of the general formula (II) or (III) with a protected monosaccharide, disaccharide or oligosaccharide that carries a trichloroacetimidate group, a halogen atom or another departing group on the $C_1$ atom,
whereby a compound of the general formula (V') or (VI'), an O-glycoside of a compound of general formula (II) or (III), is formed,

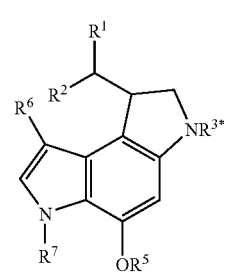
V'

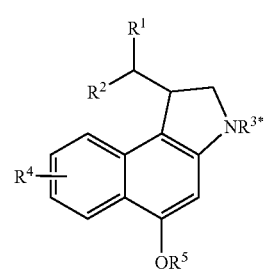
VI' wherein $R^1$, $R^2$, $R^4$, $R^5$, $R^6$, and $R^7$ are as defined in claim 5 and $R^{3*}$ has the meaning of $R^3$ and also denotes hydrogen.

9. The method of claim 8, further comprising:
reacting the compound of general formula (V') or (VI') with a heteroaromatic carboxylic acid in an organic solvent in the presence of a promoter, and for individual derivatisation steps also in the presence of a base, whereby a compound of general formula (V) or (VI) is formed,
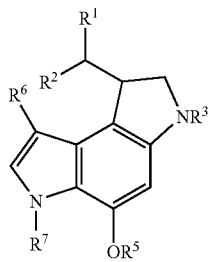
V
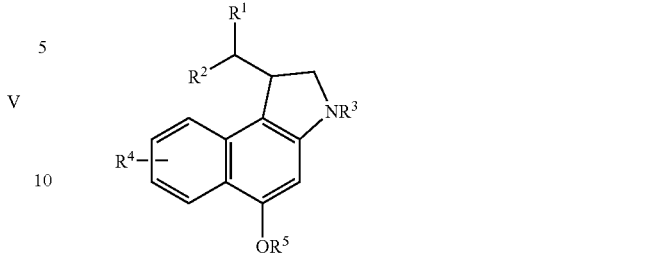
VI
wherein $R^1$, $R^2$, $R^4$, $R^5$, $R^6$ and $R^7$ are as defined in claim 1 and $R^3$ is a heteroaromatic carbonyl group.
* * * * *